(12) United States Patent
Hirayama

(10) Patent No.: US 11,395,586 B2
(45) Date of Patent: Jul. 26, 2022

(54) SUBJECTIVE OPTOMETRY APPARATUS AND STORAGE MEDIUM

(71) Applicant: NIDEK CO., LTD., Aichi (JP)

(72) Inventor: Yukito Hirayama, Aichi (JP)

(73) Assignee: NIDEK CO., LTD., Aichi (JP)

(*) Notice: Subject to any disclaimer, the term of this patent is extended or adjusted under 35 U.S.C. 154(b) by 236 days.

(21) Appl. No.: 16/527,494

(22) Filed: Jul. 31, 2019

(65) Prior Publication Data

US 2020/0037869 A1 Feb. 6, 2020

(30) Foreign Application Priority Data

Aug. 3, 2018 (JP) .............................. JP2018-146360

(51) Int. Cl.
| | |
|---|---|
| *A61B 3/02* | (2006.01) |
| *A61B 3/10* | (2006.01) |
| *A61B 3/00* | (2006.01) |
| *A61B 3/032* | (2006.01) |
| *A61B 3/028* | (2006.01) |

(52) U.S. Cl.
CPC ............ *A61B 3/032* (2013.01); *A61B 3/0091* (2013.01); *A61B 3/0285* (2013.01)

(58) Field of Classification Search
CPC .... A61B 3/00; A61B 3/08; A61B 3/10; A61B 3/14; A61B 3/02; A61B 3/0285; A61B 3/04
USPC ........ 351/234, 200, 205, 201, 206, 209–211, 351/221–223, 245–246, 233, 235
See application file for complete search history.

(56) References Cited

U.S. PATENT DOCUMENTS

| | | |
|---|---|---|
| 2015/0342455 A1 | 12/2015 | Kanazawa et al. |
| 2018/0078135 A1* | 3/2018 | Takii .................. A61B 3/111 |

(Continued)

FOREIGN PATENT DOCUMENTS

| | | |
|---|---|---|
| EP | 3 329 835 A1 | 6/2018 |
| EP | 3 533 383 A1 | 9/2019 |

(Continued)

OTHER PUBLICATIONS

Communication dated Jan. 13, 2020, issued by the European Patent Office in counterpart European Application No. 19189567.1.

(Continued)

*Primary Examiner* — Dawayne Pinkney
(74) *Attorney, Agent, or Firm* — Sughrue Mion, PLLC

(57) ABSTRACT

A subjective optometry apparatus subjectively measures optical characteristics of a subject eye. The subjective optometry apparatus includes a light projecting optical system, an optical path switching portion that switches between a first optical path having a first examination distance and a second optical path having a second examination distance, and an examination distance changing portion that optically changes the first examination distance or the second examination distance. Based on examination distance information, the examination distance changing unit causes the optical path switching portion to set an optical path to either the first optical path or the second optical path, and drives a distance changing optical member in the set optical path to optically change the examination distance to an examination distance different from the first examination distance and the second examination distance.

16 Claims, 9 Drawing Sheets

(56) References Cited

U.S. PATENT DOCUMENTS

2018/0153392 A1 6/2018 Shibata et al.
2019/0269318 A1 9/2019 Takii et al.

FOREIGN PATENT DOCUMENTS

| JP | 5-176893 A | 7/1993 |
| JP | 2015-210506 A | 11/2015 |
| JP | 2016-10679 A | 1/2016 |

OTHER PUBLICATIONS

Communication dated May 24, 2022, issued by the Japanese Patent Office in counterpart Japanese Patent Application No. 2018-146360.

* cited by examiner

SUBJECTIVE OPTOMETRY APPARATUS AND STORAGE MEDIUM

CROSS-REFERENCE TO RELATED APPLICATION

This application claims priority from Japanese Patent Application No. 2018-146360 filed on Aug. 3, 2018, the entire subject-matter of which is incorporated herein by reference.

TECHNICAL FIELD

The present disclosure relates to a subjective optometry apparatus and a storage medium storing a subjective optometry program for subjectively measuring optical characteristics of a subject eye.

BACKGROUND

A subjective optometry apparatus is known as follow. A calibration unit (for example, an optometry unit) to be disposed in front of an eye of an examinee (subject eye) is used. An optical element such as a spherical lens and a cylindrical (astigmatic) lens is disposed in an examination window of the optometry unit. Optical characteristics of the subject eye are subjectively examined (measured) by presenting a visual target to the subject eye through the disposed optical element (refer to JP-A-H5-176893). In addition, in recent years, a device is known as follows. The subjective optometry apparatus as described above is used, and an examination distance is changed to the desired examination distance so as to measure the optical characteristics of the subject eye (refer to JP-A-2016-010679).

Incidentally, in the above-described subjective optometry apparatus, studies have been carried out in order to broad a range of the examination distance which can be optionally changed. As a result, in a case where the examination distance is optically changed to the desired examination distance, it is found that a target light flux having an aberration is presented to a subject eye. That is, in a case where the examinee confirms a visual target at the optically changed examination distance, the examinee cannot sometimes satisfactorily view a visual target due to influence of the aberration (for example, the visual target is blurred). Accordingly, it is found that the visual target under a natural viewing condition cannot be presented to the examinee. In a case where a subjective examination is performed under this state, a satisfactory measurement result cannot be obtained.

SUMMARY

An object of the present disclosure is to provide a subjective optometry apparatus and a storage medium storing a subjective optometry program which can present a visual target affected having a suppressed aberration, and which can present the visual target under a natural viewing condition.

In order to solve the above-described problem, the present disclosure includes the following configurations.

(1) A subjective optometry apparatus for subjectively measuring optical characteristics of a subject eye, including:

a light projecting optical system that includes a visual target presenting portion configured to emit a target light flux and an optical member configured to guide the target light flux to the subject eye such that an image of the target light flux is optically projected on the subject eye at a first examination distance, and that is configured to project the target light flux emitted from the visual target presenting portion toward the subject eye through the optical member, the light projecting optical system projecting the target light flux on the subject eye at the first examination distance to subjectively measure the optical characteristics of the subject eye;

an optical path switching portion configured to switch between a first optical path through which the target light flux is projected on the subject eye at the first examination distance and a second optical path through which the image of the target light flux emitted from the visual target presenting portion is projected on the subject eye without passing through the optical member at a second examination distance which is different from the first examination distance;

an examination distance changing portion that includes a distance changing optical member and a driving portion configured to drive the distance changing optical member, and that is configured to optically change the first examination distance or the second examination distance by driving the distance changing optical member in any one of the first optical path and the second optical path; and an examination distance information acquisition portion configured to acquire examination distance information for setting an examination distance set when the target light flux is projected on the subject eye, in which based on the examination distance information, the examination distance changing portion causes the optical path switching portion to set an optical path through which the target light flux is projected on the subject eye to either the first optical path or the second optical path, and drives the distance changing optical member in the set optical path to optically change the examination distance to an examination distance which is different from the first examination distance and the second examination distance.

(2) A subjective optometry apparatus for subjectively measuring optical characteristics of a subject eye, including:

a light projecting optical system that includes a visual target presenting portion configured to emit a target light flux and an optical member configured to guide the target light flux to the subject eye such that an image of the target light flux is optically projected on the subject eye at a far distance examination distance, and that is configured to project the target light flux emitted from the visual target presenting portion toward the subject eye through the optical member, the light projecting optical system projecting the target light flux on the subject eye at the far distance examination distance to subjectively measure the optical characteristics of the subject eye;

an optical path switching portion configured to switch between a first optical path through which the target light flux is projected on the subject eye at the far distance examination distance and a second optical path through which the image of the target light flux emitted from the visual target presenting portion is projected on the subject eye without passing through the optical member at a near distance examination distance which is different from the far distance examination distance;

an examination distance changing portion that includes a distance changing optical member and a driving portion configured to drive the distance changing optical member, and that is configured to optically change the near distance examination distance by driving the distance changing optical member in a near distance examination optical path; and an examination distance information acquisition portion configured to acquire examination distance information for setting an examination distance set when the target light flux is projected on the subject eye, in which in a case where the examination distance information indicates an examination distance having a range of 25 cm to 65 cm, the examination distance changing portion causes the optical path switching portion to set an optical path through which the target light flux is projected on the subject eye to the near distance examination optical path, drives the distance changing optical member in the set optical path to optically change the examination distance to an examination distance within the range of 25 cm to 65 cm, which is different from the near distance examination distance, and presents the visual target having a suppressed chromatic aberration to the subject eye.

(3) A non-transitory computer readable recording medium storing a subjective optometry program used in a subjective optometry apparatus for subjectively measuring optical characteristics of a subject eye by causing a light projecting optical system to project a target light flux on the subject eye at a first examination distance, in which the subjective optometry apparatus includes:
the light projecting optical system that includes a visual target presenting portion configured to emit the target light flux and an optical member configured to guide the target light flux to the subject eye such that an image of the target light flux is optically projected on the subject eye at the first examination distance, and that is configured to project the target light flux emitted from the visual target presenting portion toward the subject eye through the optical member;
an optical path switching portion configured to switch between a first optical path through which the target light flux is projected on the subject eye at the first examination distance and a second optical path through which the image of the target light flux emitted from the visual target presenting portion is projected on the subject eye without passing through the optical member at a second examination distance which is different from the first examination distance;
a distance changing optical member; and
a driving portion configured to drive the distance changing optical member,
in which the subjective optometry program is executed by a processor of the subjective optometry apparatus to cause the subjective optometry apparatus to execute:
an examination distance information acquisition step of acquiring examination distance information for setting an examination distance set when the target light flux is projected on the subject eye; and
an examination distance change step of optically changing the first examination distance or the second examination distance by driving the distance changing optical member in any one of the first optical path and the second optical path,
in which in the examination distance change step, based on the examination distance information, the optical path switching portion sets an optical path through which the target light flux is projected on the subject eye to either the first optical path or the second optical path, and drives the distance changing optical member in the set optical path to optically change the examination distance to an examination distance which is different from the first examination distance and the second examination distance.

(4) A non-transitory computer readable recording medium storing a subjective optometry program used in a subjective optometry apparatus for subjectively measuring optical characteristics of a subject eye by causing a light projecting optical system to project a target light flux on the subject eye at a far distance examination distance, in which the subjective optometry apparatus includes:
the light projecting optical system that includes a visual target presenting portion configured to emit the target light flux and an optical member configured to guide the target light flux to the subject eye such that an image of the target light flux is optically projected on the subject eye at the far distance examination distance, and that is configured to project the target light flux emitted from the visual target presenting portion toward the subject eye through the optical member;
an optical path switching portion configured to switch between a first optical path through which the target light flux is projected on the subject eye at the far distance examination distance and a second optical path through which the image of the target light flux emitted from the visual target presenting portion is projected on the subject eye without passing through the optical member at a near distance examination distance which is different from the far distance examination distance:
a distance changing optical member; and
a driving portion configured to drive the distance changing optical member,
in which the subjective optometry program is executed by a processor of the subjective optometry apparatus to cause the subjective optometry apparatus to execute:
an examination distance information acquisition step of acquiring examination distance information for setting an examination distance set when the target light flux is projected on the subject eye; and
an examination distance change step of causing the optical path switching portion to set an optical path through which the target light flux is projected on the subject eye to a near distance examination optical path, in a case where the examination distance information indicates an examination distance having a range of 25 cm to 65 cm, driving the distance changing optical member in the set optical path to optically change the examination distance to an examination distance within the range of 25 cm to 65 cm, which is different from the near distance examination distance, and presenting the visual target having a suppressed chromatic aberration to the subject eye.

DETAILED DESCRIPTION

Overview

Figure 1A:
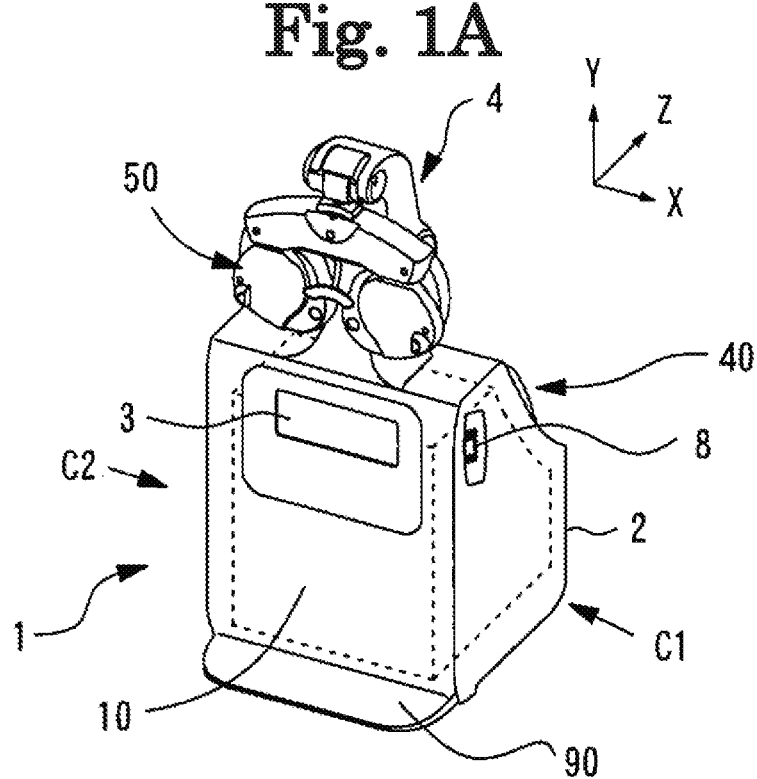
FIGS. 1A and 1B are perspective views illustrating a subjective optometry apparatus when viewed from a front surface side.

Hereinafter, an exemplary embodiment will be described with reference to the drawings. FIGS. 1 to 9 are views for describing a subjective optometry apparatus according to the present embodiment. Items classified using parentheses of < > can be used independently or in association with each other.

In the following description, a depth direction of the subjective optometry apparatus (forward-rearward direction of an examinee when the examinee is measured) will be set as a Z-direction, a horizontal direction on a plane orthogonal to the depth direction (rightward-leftward direction of the examinee when the examinee is measured) will be set as an X-direction, and a vertical direction (upward-downward direction of the examinee when the examinee is measured) will be set as a Y-direction.

The present disclosure is not limited to a device described in the present embodiment. For example, terminal control software (program) for performing functions according to the following embodiment is supplied to a system or a device via a network or various storage media. Then, a control device (for example, a CPU) of the system or the device can read and execute the program.

For example, the subjective optometry apparatus (for example, a subjective optometry apparatus 1) according to the present embodiment is used in order to subjectively measure optical characteristics of a subject eye by projecting a target light flux on the subject eye. For example, the optical characteristics of the subject eye to be subjectively measured may include at least eye refractive power (for example, spherical power, astigmatic power, and an astigmatic axis angle), contrast sensitivity, and a binocular function (for example, a heterophoria or a stereoscopic function).

In the present embodiment, for example, the subjective optometry apparatus emits has a visual target presenting portion (for example, a display 11) that emits the target light flux and an optical member (for example, a concave mirror 13) that guides the target light flux to the subject eye so that an image of the target light flux is optically projected on the subject eye at a first examination distance, and may include a light projecting optical system (for example, a light projecting optical system 10) that projects the target light flux emitted from the visual target presenting portion toward the subject eye through the optical member. For example, the subjective optometry apparatus may be used in order to subjectively measure the optical characteristics of the subject eye by causing the light projecting optical system to project the target light flux on the subject eye at the first examination distance.

For example, the subjective optometry apparatus may include an optical path switching portion (for example, a far-near distance switching portion 20) that switches between a first optical path through which the target light flux is projected on the subject eye at the first examination distance and a second optical path through which an image of the target light flux emitted from the visual target presenting portion is projected on the subject eye without passing through the optical member at a second examination distance which is different from the first examination distance. In addition, for example, the subjective optometry apparatus may have a distance changing optical member (for example, an optical element of an optometry unit 50) and a driving portion (for example, a driving portion 54 and a driving portion 55) for driving the distance changing optical member, and may include an examination distance changing portion (for example, a control portion 80) that optically changes the first examination distance or the second examination distance by driving the distance changing optical member in the optical path of either the first optical path or the second optical path. In addition, for example, the subjective optometry apparatus may include an examination distance information acquisition portion (for example, the control portion 80) that acquires examination distance information for setting an examination distance when the target light flux is projected on the subject eye. For example, based on the examination distance information, the examination distance changing portion may cause the optical path switching portion to set the optical path through which the target light flux is projected on the subject eye to either the first optical path or the second optical path. In the set optical path, the examination distance changing portion may drive the distance changing optical member so as to optically change the examination distance to an examination distance which is different from the first examination distance and the second examination distance.

As described above, for example, based on the examination distance information, the subjective optometry apparatus causes the optical path switching portion to set the optical path through which the target light flux is projected on the subject eye to either the first optical path or the second optical path, and moves the distance changing optical member with respect to the set optical path so as to change the examination distance to the examination distance which is different from the first examination distance and the second examination distance. In this manner, the optical path serving as a setting reference can be set in accordance with the examination distance, and the examination distance can be changed by driving the distance changing optical member in the set optical path. Accordingly, the visual target having a suppressed aberration can be presented. Therefore, the visual target under a natural viewing condition can be presented.

A technology according to the present disclosure can be used not only in a case where when an examination is performed on every one eye of the examinee, but also in a case where the examinations are simultaneously performed on both eyes of the examinee.

For example, the first examination distance may be a far distance examination distance, and the second examination distance may be a near distance examination distance. As a matter of course, the first examination distance and the second examination distance are not limited to the above-described configuration. For example, the first examination distance may be at least any one of the far distance examination distance (for example, 5 m), a middle distance examination distance (for example, 1 m), and the near distance examination distance (for example, 40 cm or 30 cm). That is, the first examination distance can be set to the desired examination distance, as long as the first examination distance is different from the second examination distance. In addition, for example, the second examination distance may be at least any one of the far distance examination distance, the middle distance examination distance (intermediate examination distance), and the near distance examination distance. That is, the second examination distance can be set to the desired examination distance, as long as the second examination distance is different from the first examination distance.

For example, in a case where the examination distance falls within a predetermined range in the subjective optometry apparatus, the near distance examination distance may be optically changed. In this case, for example, the subjective optometry apparatus may have the visual target presenting portion that emits the target light flux, and the optical member that guides the target light flux to the subject eye so that the image of the target light flux is optically projected on the subject eye at the far distance examination distance, and may include the light projecting optical system that projects the target light flux emitted from the visual target presenting portion toward the subject eye through the optical member. The subjective optometry apparatus may be used in order to subjectively measure the optical characteristics of the subject eye by causing the light projecting optical system to project the target light flux on the subject eye at the far distance examination distance. In addition, for example, the subjective optometry apparatus may include the optical path switching portion that switches between the first optical path through which the target light flux is projected on the subject eye at the far distance examination distance, and the second optical path through which the image of the target light flux emitted from the visual target presenting portion is projected on the subject eye without passing through the optical member at the near distance examination distance which is different from the far distance examination distance. In addition, for example, the subjective optometry apparatus may have the distance changing optical member and the driving portion for driving the distance changing optical member, and may include the examination distance changing portion that optically changes the near distance examination distance by driving the distance changing optical member in the near distance examination optical path. In addition, for example, the subjective optometry apparatus may include the examination distance information acquisition portion that acquires the examination distance information for setting the examination distance when the target light flux is projected on the subject eye. For example, in a case where the examination distance information as the examination distance information falls within a range of the examination distance of 25 cm to 65 cm, the examination distance changing portion may cause the optical path switching portion to set the optical path through which the target light flux is projected on the subject eye. In the set optical path, the examination distance changing portion may drive the distance changing optical member so as to optically change the examination distance to the examination distance falling within the range of 25 cm to 65 cm, which is the examination distance different from the near distance examination distance. In this manner, the visual target having a suppressed chromatic aberration may be presented to the subject eye. In this way, for example, in a case where the examination distance as the examination distance information falls within the range of 25 cm to 65 cm, the subjective optometry apparatus causes the optical path switching portion to set the optical path through which the target light flux is projected on the subject eye, drives the distance changing optical member in the set optical path so as to optically change the examination distance to the examination distance falling within the range of 25 cm to 65 cm, which is different from the near distance examination distance. In this manner, the visual target having the suppressed chromatic aberration is presented to the subject eye. In this manner, in a case where the examination distance to be set is 25 cm to 65 cm, the distance changing optical member can be driven in the near distance examination optical path so as to change the examination distance. Accordingly, the visual target having a suppressed chromatic aberration is presented. Therefore, the visual target under the natural viewing condition can be presented.

In the above-described configuration, the following configuration has been described as an example. Based on the examination distance information, the examination distance changing portion sets the optical path, and drives the distance changing optical member so as to optically change the examination distance. However, the present disclosure is not limited thereto. Each control may be performed in view of an inter-pupil distance (PD) of the examinee in addition to the examination distance information. In this case, for example, the subjective optometry apparatus may include an inter-pupil distance acquisition portion (for example, the control portion 80) for acquiring the inter-pupil distance of the subject eye. For example, based on the examination distance information and the inter-pupil distance, the examination distance changing portion may cause the optical path switching portion to set the optical path through which the target light flux is projected on the subject eye to either the first optical path or the second optical path, and may drive the distance changing optical member in the set optical path so as to optically change the examination distance to the examination distance which is different from the first examination distance and the second examination distance.

For example, the inter-pupil distance acquisition portion may be configured to acquire the inter-pupil distance in such a way that an examiner operates an operation portion by receiving the inter-pupil distance input to the subjective optometry apparatus. In addition, for example, the inter-pupil distance acquisition portion may be configured to acquire the inter-pupil distance by receiving the inter-pupil distance measured by a device which is different from the subjective optometry apparatus (for example, an objective optometry apparatus etc.). In addition, for example, the objective optometry apparatus may have an objective measurement portion that measures the inter-pupil distance, and may be configured to acquire the inter-pupil distance by causing an objective measurement portion to measure the inter-pupil distance of the subject eye.

For example, the examination distance changing portion may drive the distance changing optical member so as to change at least the spherical refractive power. In this manner, the examination distance changing portion may optically change the examination distance to the examination distance which is different from the first examination distance and the second examination distance. As a matter of course, for example, any configuration may be adopted, as long as the examination distance changing portion drives the distance changing optical member so that the examination distance can be changed to the examination distance which is different from the first examination distance and the second examination distance. The present disclosure is not limited only to the configuration in which the spherical refractive power is changed. For example, the examination distance changing portion may drive the distance changing optical member so as to change a prismatic amount (for example, prismatic power) together with the spherical refractive power. In this manner, the examination distance may be optically changed to the examination distance which is different from the first examination distance and the second examination. The prismatic amount to be changed may include a basal direction of a prism together with the prismatic power. For example, the prism is added thereto. In this manner, when the visual target is confirmed at the examination distance where a line of sight of the examinee is set, an optically optimal state can be reproduced, and the examination can be performed under a natural viewing condition. That is, a visual axis of the subject eye converges in accordance with the examination distance. Accordingly, the prism corresponding to the examination distance is added, thereby enabling the convergence corresponding to the examination distance can occur in the visual axis of the subject eye. Therefore, the examination can be performed under the natural viewing condition.

As described above, in a case where the examination distance changing portion changes the examination distance at least due to the spherical refractive power, a table in which the spherical refractive to be changed is set may be prepared in advance in accordance with the examination distance (examination distance information), and the prepared table may be stored in a memory (for example, a memory 82). In this case, for example, the examination distance changing portion may retrieve the spherical refractive power corresponding to the examination distance from the memory, and may drive the distance changing optical member so that the retrieved spherical refractive power is set. As a matter of course, for example, in the prepared table, the spherical refractive power to be changed may be set in accordance with the inter-pupil distance together with the examination distance. That is, for example, the table may be prepared in which the spherical refractive power to be changed is set in accordance with the examination distance and the inter-pupil distance. In addition, for example, as the spherical refractive power to be changed, an arithmetic expression for calculating the spherical refractive power for each examination distance may be stored in the memory, and the spherical refractive power may be obtained using the arithmetic expression. As a matter of course, for example, the arithmetic expression may be used in order to calculate the spherical refractive power to be changed, based on the examination distance and the inter-pupil distance.

In addition, for example, in setting any one of the first optical path and the second optical path, the examination distance changing portion may prepare in advance the table having the determined optical path set from the first optical path or the second optical path in accordance with the examination distance (examination distance information). Alternatively, the prepared table may be stored in the memory. In this case, for example, the examination distance changing portion may retrieve the optical path corresponding to the examination distance from the memory, and may cause the optical path switching portion to set the optical path so that the called optical path is set. As a matter of course, for example, in the prepared table, the optical path to be set in accordance with the inter-pupil distance together with the examination distance may be determined. That is, for example, the table may be prepared in which the optical path to be set is determined in accordance with the examination distance and the inter-pupil distance.

In addition, in a case where the examination distance is changed by the prism, the examination distance changing portion may prepare in advance the table in which the prismatic amount to be changed is set in accordance with the examination distance (examination distance information). Alternatively, the prepared table may be stored in the memory. In this case, for example, the examination distance changing portion may retrieve the prismatic amount corresponding to the examination distance from the memory, and may drive the distance changing optical member so that the retrieved prismatic amount is set. As a matter of course, for example, in the prepared table, the prismatic amount to be changed may be set in accordance with the inter-pupil distance together with the examination distance. That is, for example, the table may be prepared in which the prismatic amount to be changed is set in accordance with the examination distance and the inter-pupil distance. In addition, for example, as the prismatic amount to be changed, the arithmetic expression for calculating the prismatic amount for each examination distance may be stored in the memory, and the prismatic amount may be obtained using the arithmetic expression. As a matter of course, for example, the arithmetic expression may be used in order to calculate the prismatic amount to be changed, based on the examination distance and the inter-pupil distance.

For example, in a case where the examination distance changing portion changes the examination distance, at least two of the spherical refractive power to be changed and any one of the first optical path and the second optical path may be set in advance in combination with each other in accordance with the examination distance (examination distance information) so as to prepare the table. The prepared table may be stored in the memory. In this case, for example, the table may be prepared in which the spherical refractive power to be changed and ay one optical path of the first optical path and the second optical path are set in advance in accordance with the examination distance. The prepared table may be stored in the memory. In addition, in this case, for example, the table may be prepared in which the spherical refractive power to be changed, any one of the first optical path and the second optical path, and the prismatic amount to be changed are set in advance in accordance with the examination distance. The prepared table may be stored in the memory.

As a matter of course, for example, the table may be prepared in which at least two of the spherical refractive power to be changed, any one of the first optical path and the second optical path, and the prismatic amount to be changed are set in combination with each other in accordance with the inter-pupil distance together with the examination distance. That is, for example, the table may be prepared in which at least two of the spherical reflective power to be changed, any one of the first optical path and the second optical path, and the prismatic amount to be changed may be set in combination with each other in accordance with the examination distance and the inter-pupil distance.

In addition, for example, in a case where the examination distance changing portion changes the examination distance, the arithmetic expression for calculating at least two of the spherical refractive power to be changed, any one of the first optical path and the second optical path, and the prismatic amount to be changed may be stored in advance in accordance with the examination distance (examination distance information). The arithmetic expression may be used so as to obtain at least two of the spherical refractive power to be updated, any one of the first optical path and the second optical path, and the prismatic amount to be changed. In this case, for example, the arithmetic expression for calculating the spherical refractive power to be changed and any one of the first optical path and the second optical path in accordance with the examination distance may be stored in advance in the memory. In addition, in this case, for example, the arithmetic expression for calculating the spherical refractive power to be changed, any one of the first optical path and the second optical path, and the prismatic power to be changed in accordance with the examination distance may be stored in advance in the memory.

As a matter of course, for example, the arithmetic expression for calculating at least two of the spherical refractive power to be changed, any one of the first optical path and the second optical path, and the prismatic power to be changed, based on the examination distance and the inter-pupil distance, may be stored in the memory. The arithmetic expression may be used so as to obtain at least two of the spherical refractive power to be changed, any one of the first optical path and the second optical path, and the prismatic power to be changed.

Hereinafter, each configuration of the subjective optometry apparatus according to the present embodiment will be described in more detail.

<Light Projecting Optical System>

For example, as a visual target presenting portion, a display may be used. For example, the display may be at least one of a liquid crystal display (LCD), a liquid crystal on silicon (LCOS), an organic electro luminescence (EL). For example, the display displays an examination visual target such as a Landolt ring visual target.

In addition, for example, as the visual target presenting portion, a digital micromirror device (DMD) may be used. In general, the DMD has high reflectance, and is bright. Therefore, even in a case of using polarized light, the amount of light of the target light flux can be maintained, compared to the liquid crystal display.

In addition, for example, the visual target presenting portion may be configured to have a visual target presenting visible light source and a visual target plate. In this case, for example, the visual target plate is a rotatable disc plate and has a plurality of visual targets. For example, the plurality of targets include visual acuity test visual targets used for subjective measurement. For example, as the visual acuity test visual target, visual targets are prepared for each visual acuity value (visual acuity values 0.1, 0.3, . . . , 1.5). For example, the visual target plate is rotated by a motor, and the visual targets are switched and arranged on an optical path through which the target light flux is guided to the subject eye. As a matter of course, as the visual target presenting portion for projecting the target light flux, the visual target presenting portion having a configuration other than the above-described configuration may be used.

For example, the light projecting optical system may have at least one or more optical members for projecting the target light flux on the subject eye. For example, the projection optical system may have an optical member (for example, a concave mirror 13) for guiding the target light flux to the subject eye so that the image of the target light flux output from the visual target presenting portion is optically projected on the subject eye at the first distance.

For example, the light projecting optical system may project the target light flux on the subject eye by emitting the target light flux output from the visual target presenting portion so as to be shifted from the optical axis of the optical member. In this case, for example, the visual target presenting portion may be located by causing a normal direction to a screen of the visual target presenting portion to be inclined from the optical axis of the optical member. As a matter of course, for example, the light projecting optical system may be configured to project the target light flux on the subject eye by emitting the target light flux output from the visual target presenting portion so as to be coaxial with the optical axis of the optical member.

For example, the optical member may be at least one of a concave mirror and a lens. For example, in a case where the optical member is the concave mirror, the light projecting optical system may have a reflection member (for example, a flat mirror 12) which causes the target light flux output by the visual target presenting portion to be reflected on the concave mirror so as to guide the target light flux from the inside to the outside of the housing. According to this configuration, the number of members in the light projecting optical system can be reduced, and a space for the subjective optometry apparatus can be further reduced. As a matter of course, for example, the light projecting optical system is not limited to the above-described configuration. Any configuration may be adopted as long as the target light flux is projected on the subject eye. For example, without having the reflection member, a configuration may be adopted in which the target light flux reflected on the concave mirror is guided from the inside to the outside of the housing.

For example, as the reflection member, any one of a mirror (for example, a total reflection mirror or a half mirror) and a prism may be used. As a matter of course, without being limited thereto, the reflection member may be any member which guides the target light flux to the subject eye.

For example, in the present embodiment, the light projecting optical system may have a right eye light projecting optical system and a left eye light projecting optical system which are disposed in pair on the right and left sides. In this case, for example, a pair of right and left visual target presenting portions may be used. For example, in the right eye light projecting optical system and the left eye light projecting optical system, members configuring the right eye light projecting optical system and members configuring the left eye light projecting optical system may be configured to include the same member. In addition, for example, in the right eye light projecting optical system and the left eye light projecting optical system, at least some members of the members configuring the right eye light projecting optical system and the members configuring the left eye light projecting optical system may be configured to include a different member. For example, in the right eye light projecting optical system and the left eye light projecting optical system, at least some members of the members configuring the right eye light projecting optical system and the members configuring the left eye light projecting optical system may be configured to be shared in use. In addition, for example, in the right eye light projecting optical system and the left eye light projecting optical system, the members configuring the right eye light projecting optical system and the members configuring the left eye light projecting optical system may be configured to be provided separate from each other.

For example, in the present embodiment, the light projecting optical system may be respectively provided in accordance with the examination distance. For example, the light projecting optical system may have a light projecting optical system for the first examination distance in which the target light flux is projected on the subject eye at the first examination distance, and a light projecting optical system for the second examination distance in which the target light flux is projected on the subject eye at the second examination distance which is different from the first examination distance. In this case, for example, in the light projecting optical system for the first examination distance and the light projecting optical system for the second examination distance, at least some members of the members configuring the light projecting optical system for the first examination distance and the members the light projecting optical system for the second examination distance may be configured to be shared in use. In addition, for example, in the light projecting optical system for the first examination distance and the light projecting optical system for the second examination distance, the members configuring the light projecting optical system for the first examination distance and the members the light projecting optical system for the second examination distance may be configured to be provided separate from each other.

<Optical Path Switching Portion>

For example, the optical path switching portion may switch between the first optical path and the second optical path by inserting and removing the visual target presenting portion between the subject eye and the optical member in the first optical path. That is, the visual target presenting portion may be inserted and removed between the subject eye and the optical member in the first optical path. In this manner, the optical path switching portion may switch between the first optical path through which the examinee confirms the visual target presented by the visual target presenting portion through the optical member and the second optical path through which the examinee confirms the visual target presented by the visual target presenting portion without passing through the optical member.

In addition, for example, the optical path switching portion may switch between the first optical path and the second optical path by inserting and removing the optical member for switching the optical path between the subject eye and the optical member in the first optical path. For example, the optical member for switching the optical path may be at least one of a mirror, a lens, and a prism. As a matter of course, as the optical member for switching the optical path, the optical member different from the above-described optical member may be used. For example, the optical member for switching the optical path may be a shield member. In this case, for example, a configuration may be adopted as follows. One optical path of the first optical path and the second optical path is shielded from the target light flux, and the target light flux output from the other optical path is guided to the subject eye.

The optical path switching portion is not limited to the above-described configuration.

The optical path switching portion may be configured to switch between the first optical path and the second optical path by driving the optical member disposed in the subjective optometry apparatus.

<Examination Distance Changing Portion>

For example, the examination distance changing portion may drive the driving portion so as to move the distance changing optical member in any one of the first optical path and the second optical path. In this manner, the examination distance changing portion may optically change either the first examination distance or the second examination distance. In this way, for example, the examination distance changing portion moves the distance changing optical member with respect to the set optical path so as to change the examination distance to the examination distance which is different from the first examination distance and the second examination distance. In this manner, an easy configuration can change the examination distance.

For example, the present disclosure is not limited to the configuration in which the examination distance changing portion moves the distance changing optical member so as to optically change either the first examination distance or the second examination distance. For example, any configuration may be adopted in which an optometry distance can be optically changed, as long as the examination distance changing portion drives the distance changing optical member so as to optically change an optical position of the visual target. As an example, for example, the examination distance changing portion may drive the distance changing optical member, and may change a focal position of the distance changing optical member so as to optically change either the first examination distance or the second examination distance. In this case, for example, a variable focus lens may be used as the distance changing optical member.

For example, as a configuration for optically changing either the first examination distance or the second examination distance by moving the distance changing optical member, a configuration may be adopted in which the distance changing optical member is inserted into the optical path and is removed from the optical path. For example, the examination distance changing portion may change the examination distance by driving the driving portion to insert the distance changing optical member into the first optical path or the second optical path or to remove the distance changing optical member from the first optical path or the second optical path.

In addition, for example, as a configuration for optically changing either the first examination distance or the second examination distance by moving the distance changing optical member, the examination distance may be changed by driving the driving portion and moving the distance changing optical member in an optical axis direction of either the first optical path or the second optical path. As a matter of course, the examination distance changing portion may change the examination distance by driving the driving portion and moving the distance changing optical member in a direction different from the optical axis direction of either the first optical path or the second optical path. For example, the different direction may be an oblique direction.

For example, in setting either the first optical path or the second optical path, the examination distance changing portion may set the optical path having a smaller optical change amount changed by the distance changing optical member when either the first examination distance or the second examination distance is changed. For example, in a case of a configuration in which the examination distance changing portion optically changes the examination distance by changing at least the spherical reflective power, the examination distance changing portion may set the optical path having less spherical refractive power to be changed between the first optical path and the second optical path. In addition, for example, in a case of a configuration in which the examination distance changing portion optically changes the examination distance by changing the prismatic amount, the examination distance changing portion may set the optical path having a smaller prismatic amount to be changed between the first optical path and the second optical path. In addition, for example, in a case of a configuration in which the examination distance changing portion optically changes the examination distance by changing at least the spherical refractive power and the prismatic amount, the examination distance changing portion may change the optical path having both the less spherical refractive power to be changed and the smaller prismatic amount between the first optical path and the second optical path.

In this way, for example, in setting either the first optical path or the second optical path, the examination distance changing portion may set the optical path having a smaller optical change amount changed by the distance changing optical member when either the first examination distance or the second examination distance is change. According to this configuration, the optical change amount can be reduced, and the visual target having a more suppressed aberration can be presented.

For example, the distance changing optical member may be configured to include at least one optical member. For example, the distance changing optical member may adopt any optical member (for example, the visual target presenting portion or the optical member in the light projecting optical system) included in the light projecting optical system. In addition, for example, the distance changing optical member may be a dedicated optical member provided separate from the optical member included in the light projecting optical system.

For example, the distance changing optical member may be at least one of a lens and a prism. As a matter of course, the distance changing optical member may adopt the optical member which is different from the above-described optical member. For example, the distance changing optical member may adopt a mirror or a wavefront modulation element. For example, in a case of using a lens, at least one of a spherical lens and a non-spherical lens may be used.

<Examination Distance Information Acquisition Portion>

For example, a configuration may be adopted as follows. The examination distance information acquisition portion may acquire the examination distance information by receiving the examination distance information input to the subjective optometry apparatus by the examiner operating the operation portion (for example, a controller 81). In addition, for example, the examination distance information acquisition portion may be configured to acquire the examination distance information by receiving the examination distance information set by a device (for example, an objective optometry apparatus etc.) which is different from the subjective optometry apparatus.

For example, the examination distance information may be numerical information of the examination distance (for example, 20 cm to 5 m). In addition, for example, the examination distance information may be information relating to the examination distance.

For example, the information relating to the examination distance may be an item indicating the examination distances such as a far distance examination distance, a middle distance examination distance (intermediate examination distance), and a near distance examination distance.

<Calibration Unit>

For example, the subjective optometry apparatus may include the calibration unit (for example, an optometry unit 50) which is disposed in the optical path of the light projecting optical system and which changes the optical characteristics of the target light flux. In addition, for example, the subjective optometry apparatus may include an optical characteristic information acquisition portion (for example, the control portion 80) that acquires optical characteristic information for causing the calibration unit to change the optical characteristics of the target light flux. In addition, for example, the subjective optometry apparatus may include a calibration control portion (for example, the control portion 80) that controls the calibration unit, based on the optical characteristic information.

For example, the calibration unit may be configured to change the optical characteristics (for example, at least any one of the spherical power, the cylindrical power (astigmatic power), the astigmatic axis angle, the polarization characteristic, and the aberration amount) of the target light flux. For example, as a configuration for changing the optical characteristics of the target light flux, a configuration for controlling an optical element may be adopted. For example, as the optical element, a configuration using at least any one of a spherical lens, a cylindrical lens, a cross cylinder lens, a rotary prism, a wavefront modulation element, and a variable focus lens may be adopted. As a matter of course, for example, as the optical element, the optical element which is different from the above-described optical element may be used.

For example, the calibration unit may be configured to correct the spherical power of the subject eye by optically changing a presentation position (presentation distance) of the visual target with respect to the subject eye. In this case, for example, as a configuration in which the presentation position (presentation distance) of the visual target is optically changed, a configuration may be adopted in which a light source (for example, a display) is moved in the optical axis direction. In addition, in this case, for example, a configuration may be adopted in which the optical element (for example, the spherical lens) disposed in the optical path is moved in the optical axis direction. As a matter of course, the calibration unit may be configured so that a configuration for controlling the optical element and a configuration for moving the optical element disposed in the optical path in the optical axis direction are combined with each other.

For example, the calibration unit may be the optometry unit (phoropter) that switches and arranges the optical elements to be placed in front of the subject eye. For example, the optometry unit may be configured to include a pair of right and left lens chamber units for switching and arranging the optical elements in the examination window. For example, the optometry unit may have a lens disc in which the plurality of optical elements are arranged on the same circumference, and the driving portion for rotating the lens disc, and may be configured to electrically switch the optical elements by driving a driving portion (for example, a motor).

For example, as the calibration unit, a configuration may be adopted as follows. The optical element may be disposed between the optical member for guiding the target light flux emitted from the light projecting optical system toward the subject eye and the light source of the light projecting optical system so as to change the optical characteristics of the target light flux by controlling the optical element. That is, as the calibration unit, a configuration of a phantom lens refractometer (phantom calibration unit) may be adopted. In this case, for example, the target light flux corrected by the calibration unit is guided to the subject eye through the optical member.

For example, in the present embodiment, the calibration unit has a right-eye calibration unit and a left-eye calibration unit which are disposed in pair on the right and left sides. For example, in the right eye calibration unit and the left eye calibration unit, members configuring the right eye calibration unit and members configuring the left calibration unit may be configured to include the same member. In addition, for example, in the right eye calibration unit and the left eye calibration unit, members configuring the right eye calibration unit and members configuring the left eye calibration unit may be configured to include at least some different members. For example, in the right eye calibration unit and the left eye calibration unit, members configuring the right eye calibration unit and members configuring the left eye calibration unit may be configured so that at least some members are shared in use. In addition, for example, in the right eye calibration unit and the left eye calibration unit, members configuring the right eye calibration unit and members configuring the left eye calibration unit may be configured to be provided separate from each other.

For example, the optical characteristic information acquisition portion may be configured to acquire the optical characteristic information by receiving the optical characteristic information input to the subjective optometry apparatus by the examiner operating the operation portion. In addition, for example, the optical characteristic information acquisition portion may be configured to acquire the optical characteristic information by receiving the optical characteristic information measured by a device (for example, the objective optometry apparatus) which is different from the subjective optometry apparatus. In addition, for example, the subjective optometry apparatus may have an objective measurement portion that measures the optical characteristic information, and the objective measurement portion may be configured to acquire the optical characteristic information by measuring the optical characteristic information of the subject eye.

For example, the optical characteristic information may include at least one of the eye refractive power (for example, the spherical power, the astigmatic power, and the astigmatic axis angle), the contrast sensitivity, and the binocular function (for example, the heterophoria function or the steric function).

For example, in a case where the subjective optometry apparatus has the calibration unit, the distance changing optical member may be shared in use with the calibration unit. For example, the distance changing optical member may be configured so that at least some members configuring the calibration unit are shared in use. For example, the distance changing optical member is shared in use with the calibration unit. In this manner, the number of dedicated optical members to be separately provided can be reduced, and complicated calibration processes can be reduced. Therefore, an easy configuration can change the examination distance. In addition, the number of dedicated members is reduced, and thus, the subjective optometry apparatus having a further reduced space can be provided.

For example, in a case where the distance changing optical member is shared in use with the calibration unit, the calibration control portion may control the calibration unit, based on the optical characteristic information and the examination distance information. For example, the calibration control portion may control the calibration unit, based on the optical characteristic information and the examination distance information. In this manner, even in a case where the examination distance is changed using the calibration unit, the calibration unit can change the optical characteristics in view of a change in the examination distance. Accordingly, an easy configuration can change the examination distance, and the optical characteristics of the target light flux can be satisfactorily changed by the calibration unit.

<Housing and Holding Unit>

For example, the subjective optometry apparatus may include a housing (for example, a housing 2) that accommodates the light projecting optical system. For example, the subjective optometry apparatus may include a holding unit (for example, a holding arm 35) that holds the calibration unit. For example, in the subjective optometry apparatus, the housing and the calibration unit may be integrally connected. As an example, for example, the holding unit may be configured to integrally connect the housing and the calibration unit.

For example, in a case where the calibration unit is the optometry unit (for example, the optometry unit 50), a configuration may be adopted as follows. For example, at the examination position, an examination window (for example, an examination window 53) of the optometry unit and a presentation window (for example, a presentation window 3) of the housing may be arranged to face each other.

For example, instead of a configuration in which the housing and the calibration unit are constantly connected, the subjective optometry apparatus may be configured so that both of these are close to each other. For example, as the configuration in which both of these are arranged close to each other, a distance may exist between the optometry unit and the housing so that an examiner's head cannot enter. For example, as the configuration in which both of these are arranged close to each other, a distance between the optometry unit and the housing may be 1 m or shorter (for example, 1 m, 500 mm, 135 mm, or 70 mm). As a matter of course, for example, as the configuration in which both of these are arranged close to each other, a configuration may be adopted in which the distance between the optometry unit and the housing is longer than 1 m.

In the present embodiment, a configuration may be adopted in which the examination distance changing portion, the examination distance information acquisition portion, the optical characteristic information acquisition portion, the calibration control portion, and the inter-pupil distance acquisition portion are shared in use. In addition, for example, a configuration may be adopted in which the examination distance changing portion, the examination distance information acquisition portion, the optical characteristic information acquisition portion, the calibration control portion, and the inter-pupil distance acquisition portion are provided separate from each other. As a matter of course, each of the above-described portions may be configured to include a plurality of control portions.

Application Example

Figure 1B:
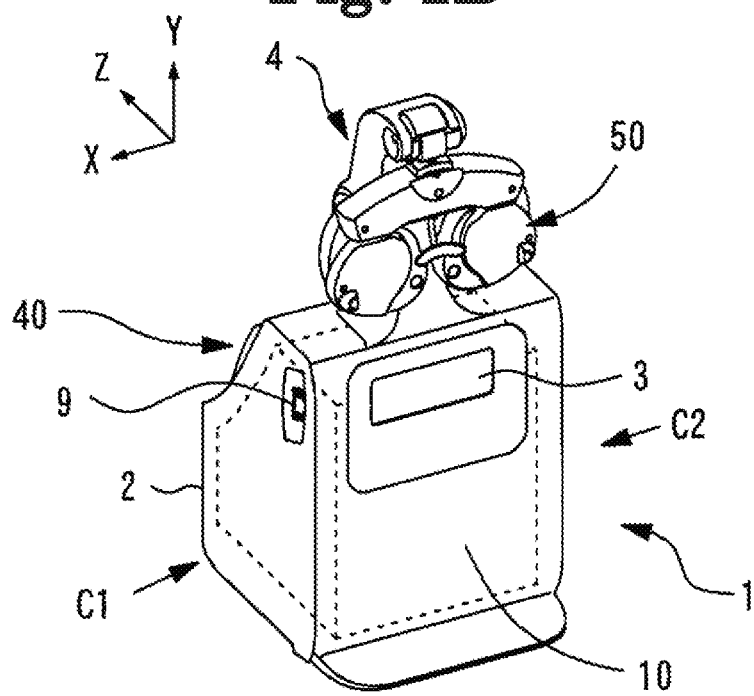
Figure 2:
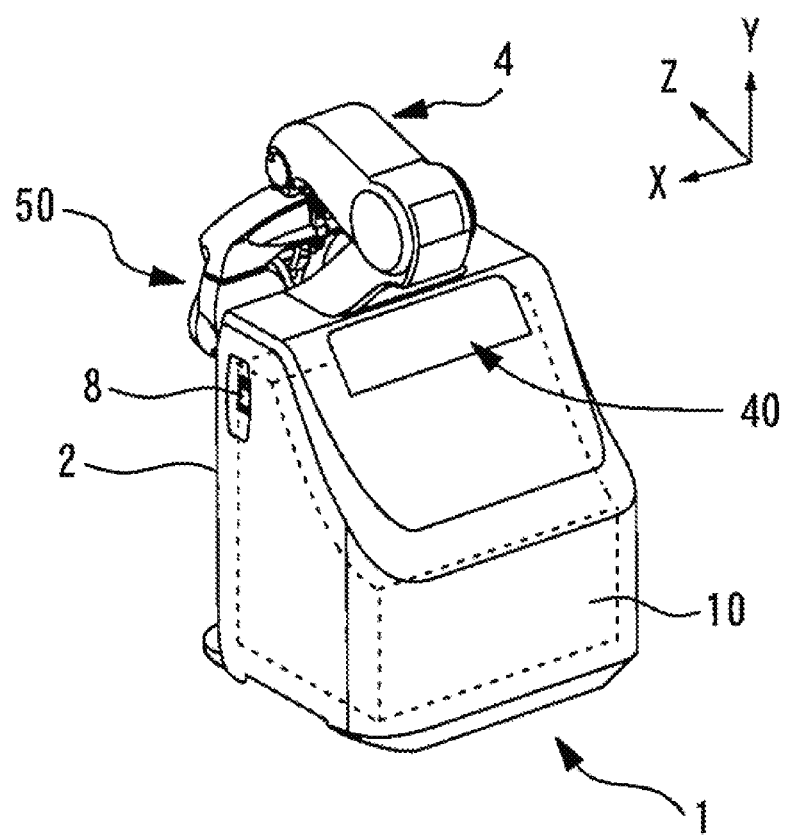
FIG. 2 is a perspective view illustrating the subjective optometry apparatus when viewed from a rear surface side.

Hereinafter, a configuration of the subjective optometry apparatus according to an application example will be described. For example, FIGS. 1A and 1B are perspective views illustrating the subjective optometry apparatus 1 when viewed from the front surface side. For example, FIG. 2 is a perspective view illustrating the subjective optometry apparatus 1 according to this application example when viewed from the rear surface side. In this application example, description will be made in such a way that a side on which a presentation window 3 (to be described later) is positioned is set as the front surface of the subjective optometry apparatus 1 and a side on which an observation window 41 (to be described later) is positioned is set as the rear surface of the subjective optometry apparatus 1. For example, FIG. 1A is a perspective view illustrating the subjective optometry apparatus 1 when viewed from the left side of the front surface. In addition, for example, FIG. 1B is a perspective view illustrating the subjective optometry apparatus 1 when viewed from the right side if the front surface.

For example, the subjective optometry apparatus 1 includes the housing 2, the presentation window 3, the holding unit 4, a first operation portion 8, a second operation portion 9, the light projecting optical system 10, an observation unit 40, and an optometry unit 50. For example, in this application example, an examinee faces the front surface of the housing 2. For example, the housing 2 internally accommodates the light projecting optical system 10. For example, the presentation window 3 is used to present an examination visual target to an eye of the examinee (hereinafter, referred to as a subject eye). For example, the presentation window 3 transmits the target light flux in the light projecting optical system 10. Therefore, the target light flux is projected on the subject eye via the presentation window 3. For example, the presentation window 3 is closed with a transparent panel in order to prevent dust from entering. For example, as the transparent panel, a transparent member such as an acrylic resin or a glass plate can be used.

In a case where the optometry unit 50 is disposed between the presentation window 3 and the subject eye, the target light flux is projected on the subject eye via the presentation window 3 and the examination window 53 of the optometry unit 50.

Figure 8:
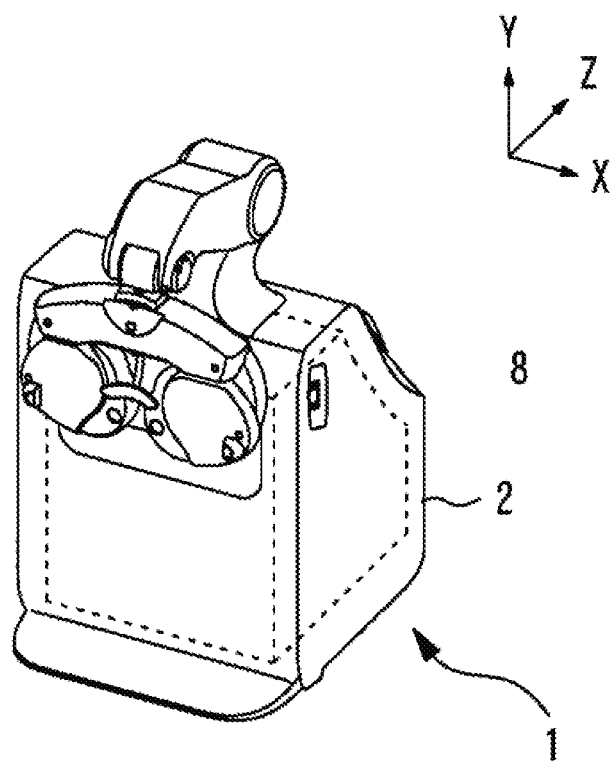
FIG. 8 is a view illustrating a state where a subjective examination using the optometry unit is available.

For example, the holding unit 4 holds the optometry unit 50. For example, the holding unit 4 supports the optometry unit 50 at a retracted position or an examination position. For example, as illustrated in FIGS. 1A and 1B, the retracted position in this application example is in a state where the optometry unit 50 is raised to an upper portion of the housing 2. In addition, as illustrated in FIG. 8, the examination position in this application example is a state where the optometry unit 50 is lowered to the front surface of the housing 2. The retracted position and the examination position are switched by a movement unit 6 (refer to FIGS. 3A and 3B) of the holding unit 4 to move a holding arm 35 (refer to FIGS. 3A and 3B) of the holding unit 4 upward and downward. In this application example, the subjective optometry apparatus 1 includes the holding unit 4 configured so that the holding arm 35 and the movement unit 6 are integrated with each other. As a matter of course, the holding arm 35 and the movement unit 6 may be provided separate from each other.

<Holding Unit>

Figure 3A:
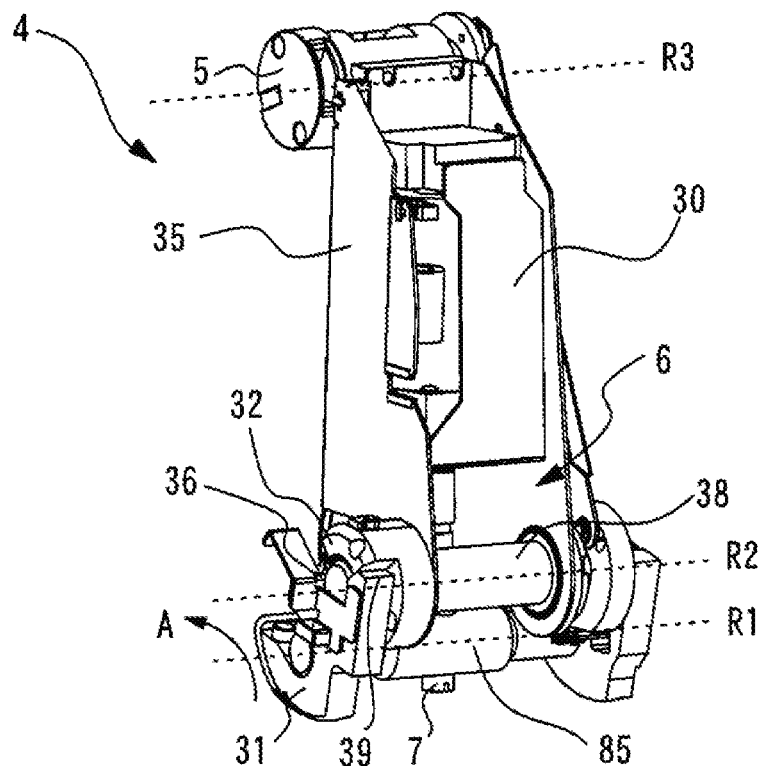
FIGS. 3A and 3B illustrate schematic views of an internal configuration in a case where an external cover of a holding unit is detached.
Figure 3B:
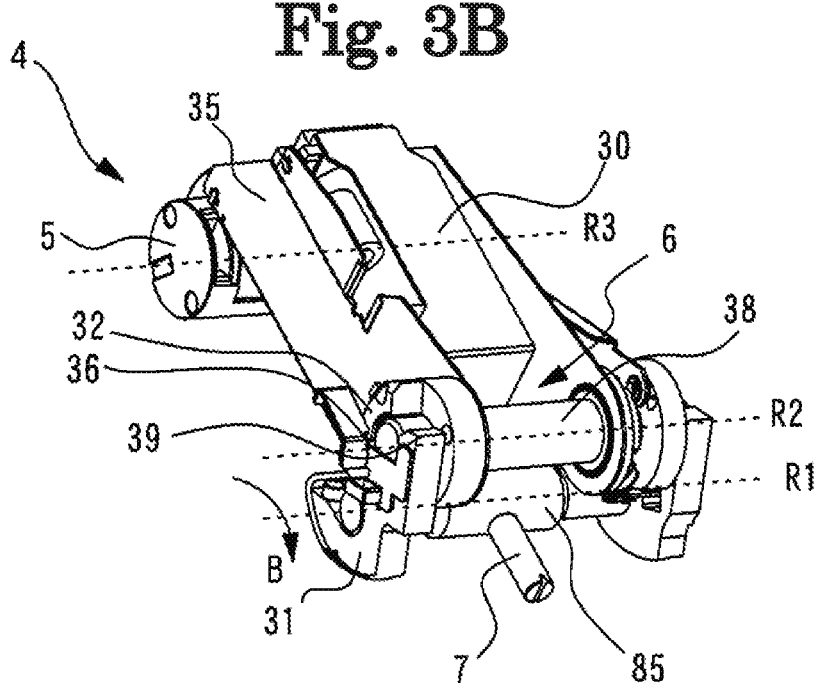

Hereinafter, the holding unit 4 will be described in detail. For example, FIGS. 3A and 3B illustrates a schematic view of an internal configuration in a case where an external cover of the holding unit 4 is detached. In FIGS. 3A and 3B, the optometry unit 50 connected to the holding arm 35 is omitted in the illustration. For example, FIG. 3A illustrates the internal configuration of the holding unit 4 in a case where the optometry unit 50 is moved to the retracted position. For example, FIG. 3B illustrates the internal configuration of the holding unit 4 in a case where the optometry unit 50 is moved to the examination position.

For example, the holding unit 4 includes a connecting portion 5, a movement unit 6, a base 31, and a holding arm 35. For example, the holding unit 4 is connected to the optometry unit 50 via the connecting portion 5. For example, the connecting portion 5 is connected to the holding arm 35 so as to be rotatable around a rotation axis R3. For example, the holding arm 35 is rotatably attached to the base 31. For example, the base 31 is disposed on an upper surface of the housing 2. For example, the base 31 is connected to the housing 2 via the connecting portion 33. For example, the base 31 is fixed to the housing 2 via the connecting portion 33. In this application example, the configuration in which the base 31 and the connecting portion 33 are provided separate from each other has been described as an example. However, this application example is not limited thereto. The base 31 and the connecting portion 33 may be configured to be integrated with each other. In this case, for example, the base 31 and the housing 2 may be connected each other.

For example, the movement unit 6 includes a driving portion (for example, a motor) 30, a shaft 7, a support member 85, a block 32, a block receiver 36, a support member 38, a block receiver 39, a detector 70, a light blocking portion 71, a long hole 72, a restriction member 75, a long hole 76, and a bearing 77. The movement unit 6 may be configured to include at least the motor 30. For example, the motor 30 is fixed to the holding arm 35, and is connected to an upper portion of the shaft 7. For example, a lower portion of the shaft 7 has a screw portion (not illustrated), and is fitted to the support member 85. That is, the support member 85 has a screw portion (not illustrated) in a penetrating portion of the shaft 7 so as to be fitted to the shaft 7. For example, the support member 85 is attached to the base 31. For example, the support member 85 supports the shaft 7 with respect to the base 31 so as to be rotatable around a rotation axis (central axis) R1 of the support member 85. For example, the holding arm 35 is attached to the base 31 by the support member 38. For example, the support member 38 supports the holding arm 35 with respect to the base 31 so as to be rotatable around a rotation axis (central axis) R2 of the support member 38.

For example, the block 32 is connected to the support member 38. For example, along with the rotation of the support member 38, the block 32 can be rotated with respect to the base 31 around the rotation axis R2 of the support member 38. For example, the block receiver 36 and the block receiver 39 are fixed to the base 31. For example, the block receiver 36 and the block receiver 39 are configured to come into contact with the block 32 at different predetermined positions. For example, in a case where the block 32 is rotated with respect to the base 31 around the rotation axis R2 of the support member 38 along with the rotation of the support member 38, if the block 32 is rotated to the predetermined position, the block 32 comes into contact with the block receiver 36 or the block receiver 39 disposed in the base 31, thereby stopping the rotation of the block 32. For example, in this application example, the block receiver 36 is configured as follows. The block receiver 36 is located at a position where the block receiver 36 and the block 32 come into contact with each other so as to stop the rotation of the block 32 in a case where the optometry unit 50 reaches the examination position from the retracted position. In addition, for example, in this application example, the block receiver 39 is configured as follows. The block receiver 39 is located at a position where the block receiver 39 and the block 32 come into contact with each other so as to stop the rotation of the block 32 in a case where the optometry unit 50 reaches the retracted position from the examination position.

For example, an operation changed from a state where the optometry unit 50 is placed at the retracted position as illustrated in FIG. 3A to a state where the optometry unit 50 is placed at the examination position as illustrated in FIG. 3B will be described. For example, the motor 30 is driven, thereby rotating the shaft 7. For example, the motor 30 is rotated forward, thereby rotating the shaft 7. The shaft 7 is rotated, thereby rotating the screw portion of the shaft 7 and moving the screw portion of the shaft 7 with respect to the support member 85 screwed to the screw portion of the shaft 7. That is, the shaft 7 moves in the axial direction of the shaft 7 with respect to the support member 85. For example, the shaft 7 moves with respect to the support member 85, and a protruding portion of the shaft 7 protruding from the support member 85 increase (shaft 7 is lengthened). For example, the support member 85 is rotated in a direction of an arrow A around the rotation axis R1 in conjunction with the increasing movement of the protruding portion of the shaft 7.

For example, since the support member 85 is rotated around the rotation axis R1, the shaft 7 is also rotated around the rotation axis R1. That is, the shaft 7 is moved in the axial direction of the shaft 7 with respect to the support member 85, and is rotated in the direction of the arrow A around the rotation axis R1. For example, since the shaft 7 is rotated, the motor 30 linked to the shaft 7 is rotated in the direction of the arrow A around the rotation axis R1. In addition, for example, the holding arm 35 having the motor 30 fixed thereto is rotated in the direction of the arrow A integrally with the rotation of the motor 30 around the rotation axis R2 of the support member 38. In this manner, the connecting portion 5 connected to the holding arm 35 is rotated in the direction of the arrow A. and the optometry unit 50 connected to the connecting portion 5 is rotated in the direction of the arrow A. In addition, for example, the connecting portion 5 is rotated with respect to the holding arm 35 so that the optometry unit 50 can maintain a vertical state by using its own weight of the optometry unit 50. In this application example, the vertical state includes a substantially vertical state. In this manner, for example, the optometry unit 50 as illustrated in FIG. 3A is moved from the retracted position, and the optometry unit 50 as illustrated in FIG. 3B is moved to the examination position. That is, the optometry unit 50 can be moved in a downward direction.

In addition, for example, the rotation (movement to the examination position) of the optometry unit 50 in the A-direction is stopped by the block 32 and the block receiver 36 when the optometry unit 50 reaches the examination position. For example, the motor 30 is driven, the block 32 is rotated in the A-direction around the rotation axis R2, and the block 32 comes into contact with the block receiver 36 when the optometry unit 50 reaches the examination position. For example, the rotation of the block 32 is stopped by coming into contact with the block receiver 36. For example, since the block 32 is stopped, the rotation of the support member 38 linked to the block 32 is stopped. In addition, as a result, the rotation of the shaft 7 and the support member 85 is also stopped. In this manner, the optometry unit 50 is stopped at the examination position. That is, the optometry unit 50 is stopped at the examination position by the block 32 and the block receiver 36.

For example, the rotation (movement to the examination position) of the optometry unit 50 in the A-direction is stopped by the block 32 and the block receiver 36 when the optometry unit 50 reaches the examination position, and thereafter, the motor 30 is continuously driven. For example, since the motor 30 is driven, the shaft 7 is rotated. However, the shaft 7 is brought into an immovable state by the block 32 and the block receiver 36. In this case, for example, the movement of the shaft 7 in the axial direction of the shaft 7 with respect to the support member 85 is stopped, and the movement of the support member 85 with respect to the shaft 7 is started. That is, driving of the motor 30 is switched from the movement of the shaft 7 to the movement of the support member 85. For example, after the movement of the support member 85 is started, if the support member 85 is moved to a predetermined position, the driving of the motor 30 is stopped.

In this way, the movement of the optometry unit 50 to the examination position is completed. For example, a switching mechanism from the movement of the shaft 7 to the movement of the support member 85 can be used as a contact suppression mechanism in a case where the optometry unit 50 comes into contact with other members when moving to the examination position.

For example, an operation changed from a state where the optometry unit 50 is placed at the examination position as illustrated in FIG. 3B to a state where the optometry unit 50 is placed at the retracted position as illustrated in FIG. 3A will be described. For example, the motor 30 is reversely rotated, thereby rotating the shaft 7. The shaft 7 is rotated. Accordingly, for example, the shaft 7 moves in the axial direction of the shaft 7 with respect to the support member 85, and the protruding portion of the shaft 7 protruding from the support member 85 decreases (shaft 7 is shortened). For example, the support member 85 is rotated in a direction of an arrow B around the rotation axis R1 in conjunction with the decreasing movement of the shaft 7. Similarly to the above description, since the support member 85 is rotated around the rotation axis R1, the connecting portion 5 connected to the holding arm 35 is rotated around the rotation axis R2 in the direction of the arrow B, and the optometry unit 50 connected to the connecting portion 5 is rotated in the direction of the arrow B. In addition, for example, the connecting portion 5 is rotated with respect to the holding arm 35 so that the optometry unit 50 can maintain a vertical state by using its own weight of the optometry unit 50. In this manner, for example, the optometry unit 50 as illustrated in FIG. 3B is moved from the examination position, and the optometry unit 50 as illustrated in FIG. 3A is moved to the retracted position. That is, the optometry unit 50 can be moved in an upward direction.

In addition, for example, the rotation (movement to the retracted position) of the optometry unit 50 in the B-direction is stopped by the block 32 and the block receiver 39 when the optometry unit 50 reaches the retracted position. For example, the motor 30 is driven, the block 32 is rotated in the B-direction around the rotation axis R2, and the block 32 comes into contact with the block receiver 39 when the optometry unit 50 reaches the retracted position. For example, the rotation of the block 32 is stopped by coming into contact with the block receiver 39. For example, since the block 32 is stopped, the rotation of the support member 38 connected to the block 32 is stopped. In addition, as a result, the rotation of the shaft 7 and the support member 85 is also stopped. In this manner, the optometry unit 50 is stopped at the retracted position. That is, the optometry unit 50 is stopped at the retracted position by the block 32 and the block receiver 39. In this way, the movement of the optometry unit 50 to the retracted position is completed.

In this application example, a configuration in which the movement of the optometry unit 50 to the retracted position is stopped by the block 32 and the block receiver 39 has been described as an example. However, this application example is not limited thereto. For example, a detection portion for detecting a retracted state may be provided so as to stop the movement of the optometry unit 50 to the retracted position, based on a detection result. In this case, as an example, for example, a shield portion is disposed in the support member 38, and the detector is disposed in the base 31. For example, in a case where the optometry unit 50 is placed at the retracted position, and in a case where the shield portion disposed in the support member 38 is detected by the detector, the movement of the optometry unit 50 to the retracted position may be stopped.

<First Operation Portion and Second Operation Portion>

Hereinafter, the first operation portion 8 and the second operation portion 9 will be described. For example, the first operation portion 8 is an upward-downward movement switch (movement switch of the optometry unit 50). In addition, for example, the second operation portion 9 is an upward-downward movement switch (movement switch of the optometry unit 50). That is, in this application example, the first operation portion 8 and the second operation portion 9 are the operation portions for performing the same operation. For example, the first operation portion 8 or the second operation portion 9 is operated. In this manner, the optometry unit 50 can be moved between the examination position in front of the subject eye and the retracted position.

For example, the first operation portion 8 is provided on the left side surface of the housing 2. For example, the second operation portion 9 is provided on the right side surface of the housing 2. For example, the first operation portion and the second operation portion are arranged above the right and left side surfaces. In this application example, for example, the first operation portion and the second operation portion are arranged at right and left symmetrical positions, based on the center of the housing 2.

In this application example, for example, the first operation portion 8 and the second operation portion 9 are the operation portions having the same shape. For example, the first operation portion 8 and the second operation portion 9 have the same shape. Accordingly, when one of the first operation portion 8 or the second operation portion 9 is operated, the subjective optometry apparatus 1 can be operated by performing an operation similar to the other operation. Therefore, it is possible to prevent a possibility that an examiner may perform an incorrect operation, and thus, the subjective optometry apparatus 1 is likely to be operated.

In this application example, as the operation portion for moving the optometry unit 50 between the examination position in front of the subject eye and the retracted position, a configuration having the first operation portion 8 and the second operation portion 9 has been described. However, the present disclosure is not limited thereto. For example, as the operation portion for moving the optometry unit 50 between the examination position in front of the subject eye and the retracted position, a configuration having at least one or more operation portions may be adopted. As an example, in a case of using one operation portion, the operation portion may be provided at a position where the operation can be performed from the right and left sides of the subjective optometry apparatus 1.

<Light Projecting Optical System>

Figure 4A:
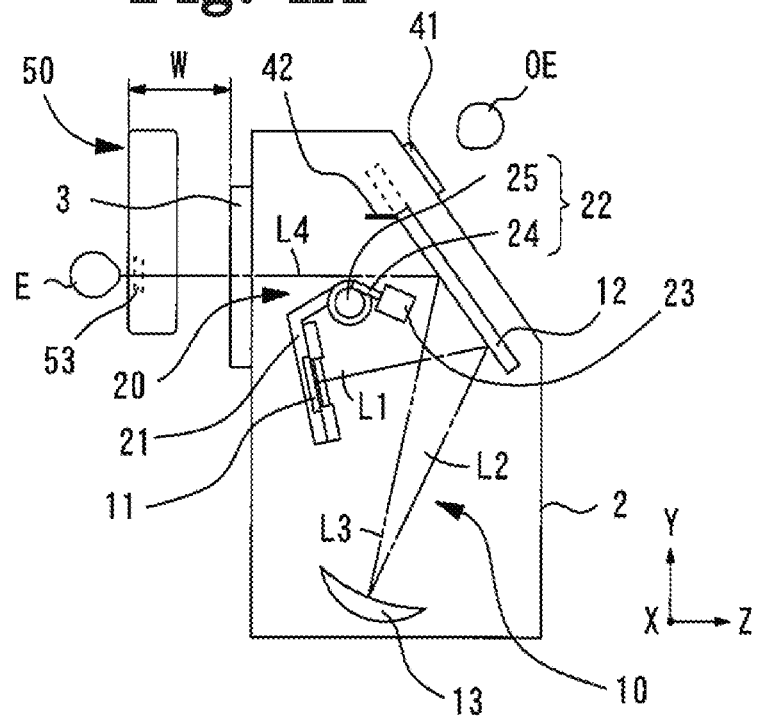
FIGS. 4A and 4B are views when a light projecting optical system is viewed from a left side surface.
Figure 4B:
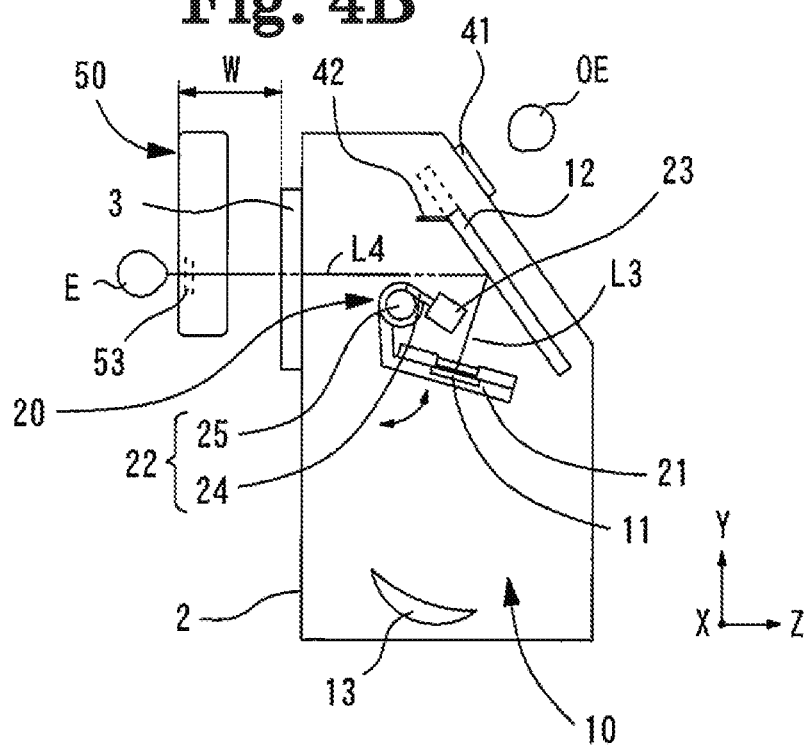

Hereinafter, the light projecting optical system 10 will be described. For example, FIGS. 4A and 4B is a view when the light projecting optical system 10 is viewed from the left side surface (arrow direction C1 in FIGS. 1A and 1B). FIG. 4A illustrates an optical arrangement at the time of a far distance examination. FIG. 4B illustrates an optical arrangement at the time of a near distance examination. For example, the light projecting optical system 10 has the visual target presenting portion, and projects the target light flux output from the visual target presenting portion on a subject eye E. For example, in this application example, a display (for example, a display 11) is used as the visual target presenting portion. For example, the light projecting optical system 10 includes the display 11, the flat mirror 12, the concave mirror 13, and a far-near distance switching portion 20.

For example, the display 11 displays the examination visual target such as a Landolt ring visual target and a fixation visual target. For example, the display on the display 11 is controlled by a control portion 80 (to be described later). For example, as the display, a liquid crystal display (LCD), an organic electro luminescence (EL), and a plasma display may be used.

For example, at the time of the far distance examination illustrated in FIG. 4A, a screen of the display 11 is directed rearward of the housing 2, and the target light flux is output in a rearward direction. The target light flux may be output from the display in a horizontal direction (Z-direction), or may be output in an oblique direction (YZ-direction). For example, at the time of the near distance examination illustrated in FIG. 4B, the screen of the display 11 is directed upward, and the target light flux is output in an upward direction. The target light flux may be output from the display in a vertical direction (Y-direction), or may be output in the oblique direction (YZ-direction). In this way, the target light flux output from the display 11 is projected on the subject eye E.

For example, the flat mirror 12 reflects the target light flux from the display 11, and guides the target light flux to the concave mirror 13. In addition, for example, the flat mirror 12 reflects the target light flux from the display 11, and guides the target light flux to the subject eye E. For example, only a lower portion (solid line portion of the flat mirror 12 in FIGS. 4A and 4B) of the flat mirror 12 is subjected to mirror coating, and an upper portion (dotted line portion of the flat mirror 12 in FIGS. 4A and 4B) of the flat mirror 12 is not subjected to the mirror coating.

Therefore, in this application example, the upper portion of the flat mirror 12 is configured to be transparent. For example, a focal distance of the flat mirror 12 at the time of the near distance examination is designed so that an optical distance from the display to the subject eye E is 40 cm. In this application example, as long as the target light flux can be reflected, this application example is not limited to the configuration using the flat mirror. For example, any reflection member may be used. In this case, for example, a configuration using a prism, a beam splitter, or a half mirror may be adopted.

For example, the concave mirror 13 reflects the target light flux from the display 11 toward the flat mirror 12. For example, in the concave mirror 13, a presentation distance of the examination visual target displayed on the display 11 is set to a far distance examination distance. For example, the focal distance of the concave mirror 13 is designed so that the optical distance from the display 11 to the subject eye E is 5 m. This application example is not limited to the configuration using the concave mirror 13. For example, any reflection member which can reflect the target light flux may be used. In this case, for example, a configuration using an aspheric mirror or a free curved surface mirror may be adopted. In addition, for example, a configuration using the lens may be adopted. In this case, for example, a configuration may be adopted as follows. The target light flux is projected on the subject eye E from the display 11 through the lens. In this manner, the optical distance from the display 11 to the subject eye E is designed to be 5 m.

For example, at the time of the far distance examination illustrated in FIG. 4A, the target light flux output from the display 11 and passing through the optical members of the flat mirror 12, the concave mirror 13, and the flat mirror 12 in this order is projected on the subject eye E. That is, if the target light flux output from the display 11 is incident on the flat mirror 12 through an optical axis L1, the target light flux is reflected in a direction of an optical axis L2, and is guided to the concave mirror 13. If the target light flux is incident on the concave mirror 13, the target light flux is reflected in a direction of an optical axis L3, and is guided to the flat mirror 12. Furthermore, if the target light flux is incident on the flat mirror 12, the target light flux is reflected in a direction of an optical axis L4, and is projected on the subject eye E of the examinee. In addition, for example, at the time of the near distance examination illustrated in FIG. 4B, the target light flux output from the display 11 and reflected on the flat mirror 12 is projected on the subject eye of the examinee. That is, the target light flux output from the display 11 is incident on the flat mirror 12 through the optical axis L3, is reflected in the direction of the optical axis L4, and is projected on the subject eye E of the examinee.

For example, in this way, the light projecting optical system 10 emits the target light flux from the inside to the outside of the housing 2.

For example, the far-near distance switching portion 20 is used in order to switch between a far distance examination optical path at the time of the far distance examination and a near distance examination optical path at the time of the near distance examination. For example, in the far distance examination optical path, the target light flux output from the display 11 is projected on the subject eye through the concave mirror 13 so that the target light flux is projected on the subject eye at the far distance examination distance. In addition, for example, in the near distance examination optical path, an image of the target light flux output from the display 11 is projected on the subject eye at the near distance examination distance without interposing the concave mirror 13 therebetween.

For example, the far-near distance switching portion 20 changes a position of the display 11 at the time of the far distance examination and at the time of the near distance examination. For example, the far-near distance switching portion 20 includes a holding portion 21, a gear 22, and a motor 23. For example, the holding portion 21 holds the display 11. For example, the gear 22 has a worm portion 24 and a wheel portion 25. For example, the worm portion 24 and the wheel portion 25 are formed using gears meshing with each other. For example, the motor 23 is connected to the worm portion 24, and the holding portion 21 is connected to the wheel portion 25. For example, as the motor 23 is driven, the worm portion 24 is rotated. In response thereto, the wheel portion 25 is rotated in an arrow direction. In this manner, the display 11 can be moved integrally with the holding portion 21, and the presentation position of the examination visual target displayed on the screen of the display 11 can be switched at the time of the far distance examination and at the time of the near distance examination. The gear 22 and the motor 23 are arranged on the side wall of the housing 2, and are arranged at positions which do not interfere with the target light flux guided from the display 11 to the subject eye E.

In this application example, a configuration in which the optical axis L3 and the optical axis L4 of the light projecting optical system 10 are coaxial with each other at the time of the far distance examination and at the time of the near distance examination has been described as an example. However, this application is not limited thereto. For example, in this application example, any configuration may be adopted as long as the target light flux can be guided to the subject eye E. Alternatively, the target light flux may pass through mutually different optical paths at the time of the far distance examination and at the time of the near distance examination.

<Observation Unit>

Figure 5:
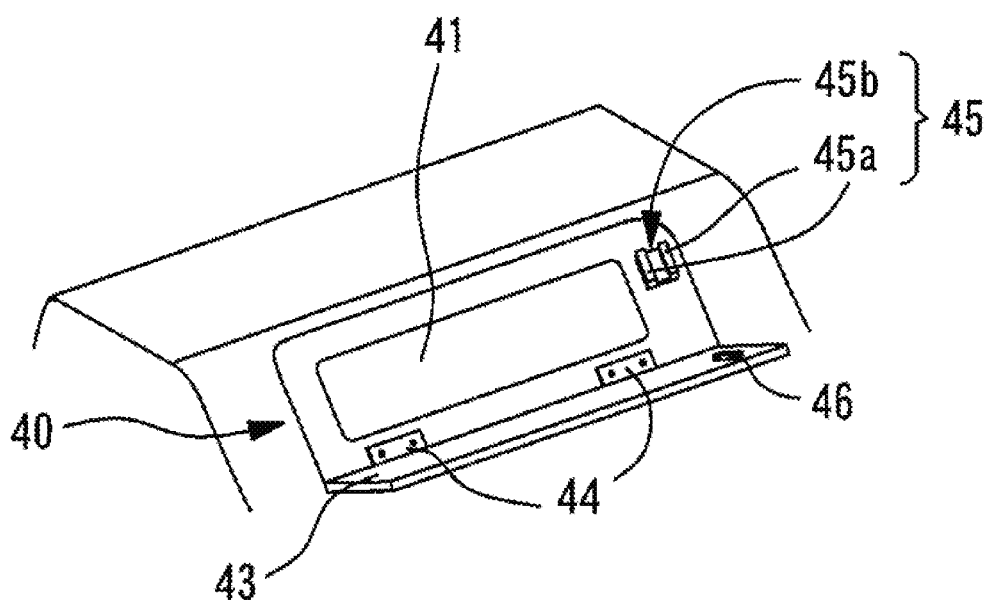
FIG. 5 is a view for describing an observation unit.

Hereinafter, the observation unit 40 will be described. FIG. 5 is a view for describing the observation unit 40. For example, the observation unit 40 in this application example is used in order to observe a positional relationship (to be described later) between the optometry unit 50 and the subject eye E via the presentation window 3. For example, in this application example, the observation unit 40 includes an observation window 41, a shield portion 42, a cover 43, and a detector (detection portion) 45. The observation unit 40 may be configured to include at least the observation window 41.

For example, the observation window 41 is used in order to observe the positional relationship between the optometry unit 50 and the subject eye E from outside the housing 2 via the presentation window 3. For example, the observation window 41 in this application example is provided at a position where an examiner's eye OE can confirm the pupil position of the subject eye E. For example, in a case where an examiner looks into the observation window 41, the flat mirror 12 is formed to be transparent in a region through which the examiner's line of sight passes so that the examiner's line of sight is not blocked by the flat mirror 12. For example, the shield portion 42 prevents the target light flux output from the light projecting optical system 10 from entering the observation window 41. For example, in this application example, the shield portion 42 is disposed at a boundary between a transparent portion and a mirror portion in the flat mirror 12.

For example, the cover 43 is fixed to the housing 2 by a hinge 44, and can be opened and closed with respect to the observation window 41. For example, the cover 43 can be opened and closed by the examiner who pushes and pulls a knob (not illustrated).

For example, the detector 45 detects the opening and closing of the cover 43 in the observation unit 40. For example, the detector 45 is configured to use an optical sensor such as a photo interrupter. That is, the detector 45 in this application example has a projection portion 45a in which a light emitting element and a light receiving element face each other, and a protruding portion 46 disposed in the cover 43 is fitted into a recess portion 45b. For example, if the light from the light emitting element is blocked by the protruding portion 46 fitted to the recess portion 45b, the detector 45 detects that the cover is in a closed state. In addition, for example, if the protruding portion 46 is separated from the recess portion 45b and the light from the light emitting element is received by the light receiving element, the detector 45 detects that the cover is in an open state.

<Optometry Unit>

Hereinafter, the optometry unit 50 will be described. For example, the optometry unit 50 is close to the housing 2 (refer to FIGS. 4A and 4B). For example, in this application example, a distance W (refer to FIGS. 4A and 4B) from the examination window 53 in the optometry unit 50 to the presentation window 3 disposed in the housing 2 is designed to be approximately 135 mm. The distance W from the examination window 53 to the presentation window 3 is not limited to this application example. For example, in a case where the distance W is shorter than a head length of an examiner, the examiner cannot insert his or her head between the optometry unit 50 and the housing 2. Accordingly, the examiner is less likely to observe the positional relationship between the optometry unit 50 and the subject eye E. Therefore, in a case where the distance W is shorter than the head length of the examiner, the observation window 41 can be effectively used.

Figure 6:
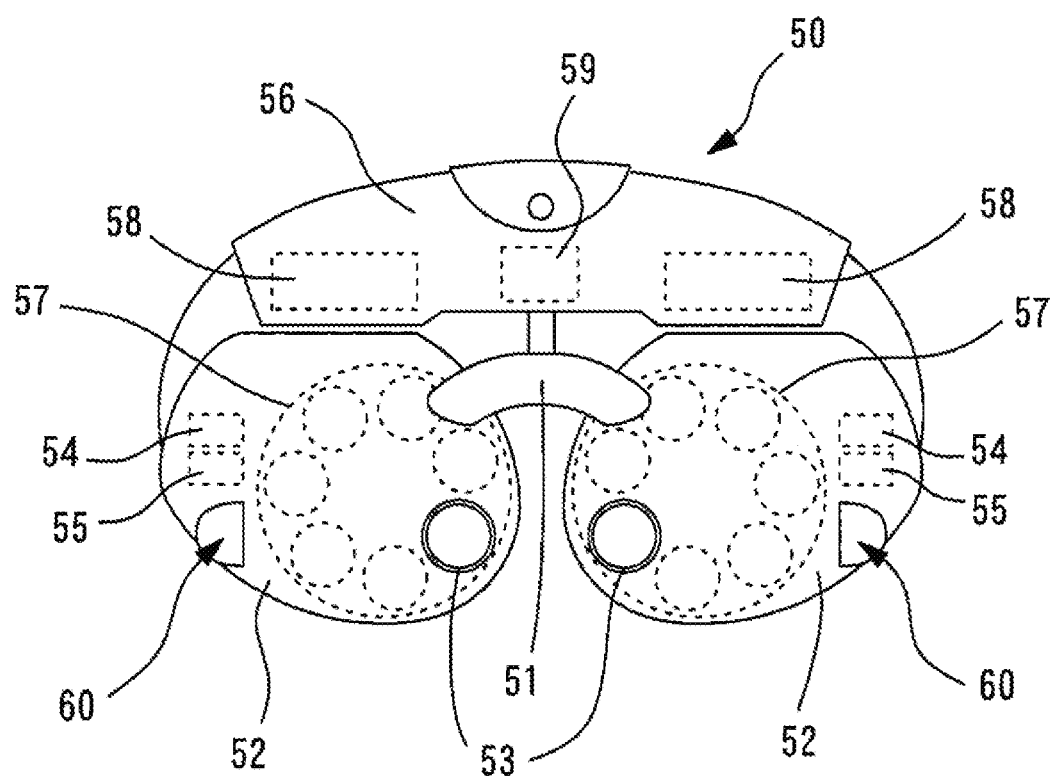
FIG. 6 is a view illustrating an optometry unit.

For example, FIG. 6 is a view illustrating the optometry unit 50. For example, the optometry unit 50 includes a forehead band 51, a pair of right and left lens chamber units 52, the examination window 53, a driving portion 54, a driving portion 55, a movement unit 56, and a corneal position aligning optical system 60. For example, the forehead band 51 comes into contact with the forehead of the examinee, and is used in order to maintain a constant distance between the subject eye E and the optometry unit 50.

For example, the lens chamber unit 52 provides any optical element at the examination window 53 so as to switch the optical elements. For example, the lens disc 57 is included inside the lens chamber unit 52. In the lens disc 57, multiple optical elements (spherical lens, cylinder lens, and dispersive prism) are arranged on the same circumference. For example, the lens disc 57 is rotationally controlled by the driving portion 54 (actuator). In this manner, the optical elements desired by the examiner are arranged in the examination window 53. For example, the optical elements arranged in the examination window 53 are rotationally controlled by the driving portion 55 (motor or solenoid). In this manner, the optical elements are arranged in the examination window 53 at a rotation angle desired by the examiner.

For example, the lens disc 57 is formed using one lens disc or a plurality of lens discs. For example, in a case where the plurality of lens discs (lens disc group) are provided, driving portions corresponding to the respective lens discs are respectively provided. For example, the respective lens discs of the lens disc group include an aperture (or a lens of OD) and a plurality of optical elements. As a type of each lens disc, a spherical lens disc having a plurality of spherical lenses having different degrees of power, a cylinder lens disc having a plurality of cylinder lenses having different degrees of power, and an auxiliary lens disc are representatively used. In addition, the lens disc in this application example includes an alignment lens having crosshairs. For example, the auxiliary lens disc has at least one of a red filter/green filter, a prism, a cross cylinder lens, a polarizer, a Maddox lens, and an auto cross cylinder lens. For a detailed configuration of the lens disc, refer to JP-A-2007-68574 and JP-A-2011-72431.

For example, the movement unit 56 adjusts an interval between the lens chamber units 52. For example, the interval between the right and left lens chamber units is adjusted by the driving portion 58 having a slide mechanism. In this manner, the interval between the examination windows 53 can be changed in accordance with PD of the subject eye. In addition, the movement unit 56 adjusts a convergence angle (inset angle) of the right and left lens chamber units. For example, the convergence angle of the right and left optometry units is adjusted by the driving portion 59 having a convergence mechanism. In addition, for a detailed configuration of the movement unit, refer to JP-A-2004-329345.

The optometry unit 50 is not limited to the above-described configuration. For example, the optometry unit 50 may be configured to change the optical characteristics (for example, at least one of the spherical power, the cylindrical power, the cylindrical axis, the polarization characteristics, and the aberration amount) of the target light flux. For example, as a configuration for changing the optical characteristics of the target light flux, a configuration for controlling the optical elements may be adopted. For example, a configuration using the wavefront modulation element and the variable focus lens may be adopted.

For example, in this application example, as the distance changing optical member, the lens disc 57 (optical element of the lens disc 57) of the optometry unit 50 is used. That is, for example, in this application example, the configuration of the optometry unit 50 is also used as the distance changing optical member for changing the examination distance and calibration unit for changing the optical characteristics of the target light flux. In this case, for example, the lens disc 57 is driven by driving at least one of the driving portion 54 and the driving portion 55. That is, the distance changing optical member is driven by driving at least one of the driving portion 54 and the driving portion 55.

In this application example, a configuration in which the configuration of the optometry unit 50 is also used as the distance changing optical member has been described as an example. However, the application example is not limited thereto. A dedicated distance changing optical member may be separately provided, or another optical member in the light projecting optical system 10 may be shared in use. In this application example, for example, the distance changing optical member includes an example of a configuration in which the distance changing optical member is disposed between the flat mirror 12 and the subject eye. As a matter of course, an arrangement position of the distance changing optical member is not limited to the above-described position as long as the examination distance can be optically changed.

<Control Portion>

Figure 7:
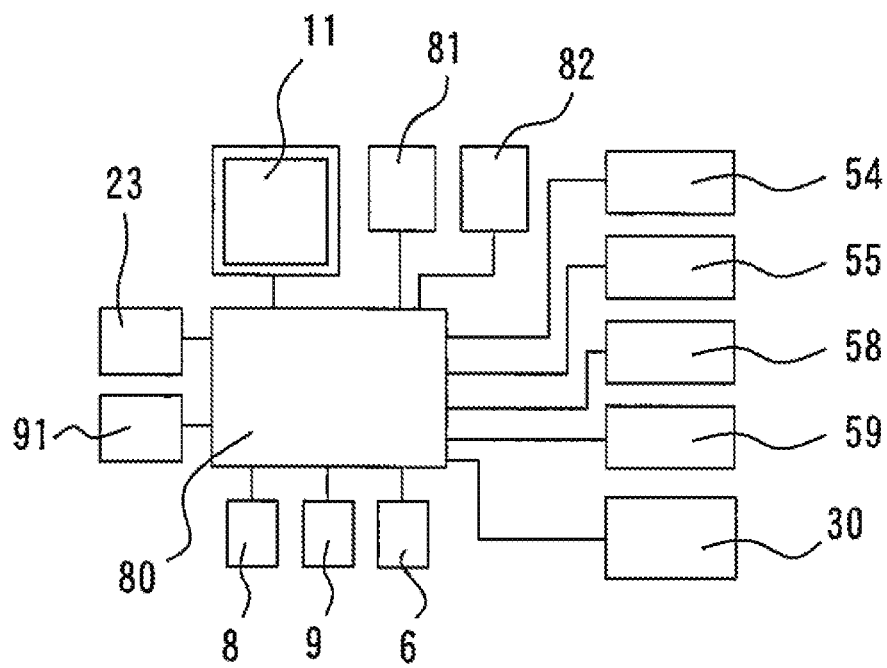
FIG. 7 is a schematic configuration diagram of a control system in the subjective optometry apparatus.

For example, FIG. 7 is a schematic block diagram of a control system in the subjective optometry apparatus 1. For example, the first operation portion 8, the second operation portion 9, the display 11, the detector 45, the controller 81, a nonvolatile memory 82, and a light source 91 are connected to the control portion 80. In addition, for example, a motor 30 included in the movement unit 6, the motor 23 included in the far-near distance switching portion 20, and driving portions (driving portions 54, 55, 58, and 59) included in respective members of the optometry unit 50 are connected to the control portion 80.

For example, the control portion 80 includes a CPU (processor), a RAM, and a ROM. For example, the CPU is responsible for controlling each member in the subjective optometry apparatus 1. For example, the RAM temporarily stores various types of information. For example, the ROM stores various programs for controlling the operations of the subjective optometry apparatus 1 or examination visual target data. The control portion 80 may be configured to include a plurality of control portions (that is, a plurality of processors).

For example, the controller 81 is used when switching displays of the display 11 in the light projecting optical system 10 or arrangements of the optical elements in the optometry unit 50. For example, a signal input from the controller 81 is input to the control portion 80 via a cable (not illustrated). In this application example, a configuration may be adopted so that the signal from the controller 81 is input to the control portion 80 via wireless communication using infrared.

For example, the nonvolatile memory 82 is a non-transitory storage medium which can hold stored contents even when power supply is shut off. For example, as the nonvolatile memory 82, a hard disk drive, a flash ROM, the subjective optometry apparatus, or a USB memory can be used. For example, the nonvolatile memory 82 stores multiple items of the examination visual target data (for example, visual target data of visual acuity values 0.1 to 2.0) such as Landolt ring visual targets.

In addition, for example, depending on the examination distance to be set and the distance between the pupils of the examinee, the nonvolatile memory 82 stores a table for setting the optical path (optical path of either the far distance examination optical path or the near distance examination optical path), the spherical refractive power (spherical power), and the prism amount (prism power and base direction of the prism) (details will be described later).

For example, in this application example, the control portion 80 switches measurement modes of the subjective optometry apparatus 1, based on a detection result of the detector 45. For example, in this application example, the control portion 80 automatically switches the measurement modes in conjunction with the opening and closing of the cover 43. For example, if the detector 45 detects that the cover 43 is open, the control portion 80 sets the measurement mode to a second mode for confirming the pupil position of the examinee. In addition, for example, if the detector 45 detects that the cover 43 is closed, the control portion 80 sets the measurement mode to a first mode for performing the subjective examination of the examinee. In this application example, a configuration is adopted so that the measurement modes are automatically switched in conjunction with opening and closing of the cover 43. However, this application example is not limited thereto. For example, the measurement modes may be manually switched by the examiner. In this case, a configuration may be adopted in which a signal for switching the measurement modes is input to the control portion 80 by using the controller 81 (to be described later).

For example, in this application example, the control portion 80 switches among a far distance examination mode for performing the subjective examination at the far distance examination distance, a near distance examination mode for performing the subjective examination at the near distance examination distance, and a desired distance examination mode for performing the subjective examination at an examination distance desired by the examiner. For example, the examination modes for changing the examination distance may be manually switched by the examiner. In this case, a configuration may be adopted in which a signal for switching the examination mode is input to the control portion 80 by using the controller 81 (to be described later). As a matter of course, a configuration may be adopted as follows. The examination may be performed sequentially at different examination distances, and the examination modes may be automatically switched.

<Examination Operation>

An examination operation of the subjective optometry apparatus 1 having the above-described configuration will be described. In this application example, a case where the desired examination distance is set so as to perform the subjective examination will be described as an example.

First, for example, the examiner operates the first operation portion 8 so as to lower the optometry unit 50 to the examination position illustrated in FIG. 8. For example, if the first operation portion 8 is operated, the control portion 80 drives the motor 30. For example, the motor 30 is driven, thereby lowering the optometry unit 50 toward the examination position. For example, if the optometry unit 50 is moved to the examination position by driving the motor 30, the block 32 and the block receiver 36 come into contact with each other, thereby stopping the lowering of the optometry unit 50. In addition, if the optometry unit 50 stops, the support member 85 starts to move, and the support member 85 is moved to a predetermined position, the driving of the motor 30 is stopped. In this manner, as illustrated in FIG. 8, the optometry unit 50 is completely moved to the examination position, and the subjective optometry apparatus 1 is in a state where the subjective examination using the optometry unit 50 can be performed.

As described above, the optometry unit 50 is moved to the examination position. Subsequently, for example, the examiner measures the PD of the examinee in advance before performing the subjective examination, and inputs the measured PD in the subjective optometry apparatus 1. In this manner, the control portion 80 drives the driving portion 58, adjusts the interval between the right and left lens chamber units 52, and changes the interval between the examination windows 53 in accordance with the PD of the subject eye. For example, the control portion 80 adjusts the interval so that the distance in the horizontal direction (X-direction) between the optical axes of the right and left examination windows 53 is identical to the PD. In this application example, the term of identical includes substantially identical.

Subsequently, the examiner instructs the examinee to look into the examination window 53. Here, for example, the examiner opens the cover 43 in order to confirm the interpupil distance PD of the subject eye E. In this case, the detector 45 detects that the cover 43 is open, and the control portion 80 switches the measurement mode to the second mode for confirming the pupil position of the examinee.

For example, if necessary, the examiner operates the controller 81 so as to adjust the interval between the right and left lens chamber units 52. Thereafter, the examiner aligns the subject eye E with the optometry unit 50 by using a corneal position aligning optical system 60 in order to confirm a corneal apex position of the subject eye E.

For example, if the subject eye E is completely aligned with the optometry unit 50, the examiner closes the cover 43, and starts the subjective examination. In this case, the control portion 80 causes the detector 45 to detect that the cover 43 is closed, and switches the measurement mode to the first mode for performing the subjective examination of the examinee.

For example, if the controller 81 is operated by the examiner and the desired distance examination mode for performing the subjective examination in the desired examination distance is selected, the examiner performs setting for the subjective examination at the desired examination distance.

For example, if the desired distance examination mode is selected, an input screen (not illustrated) for inputting the examination distance is displayed. For example, the examiner operates the controller 81, and inputs the desired examination distance. For example, if the examination distance is input, the control portion 80 controls the movement of the display 11 in accordance with the input examination distance and the inter-pupil distance PD of the subject eye E, and sets any one of the far distance examination optical path and the near distance examination optical path. In addition, for example, the control portion 80 sets the optical path, and controls the optical element of the optometry unit 50 (lens disc 57), in accordance with the input examination distance and the inter-pupil distance PD of the subject eye E. In this manner, the control portion 80 optically changes the optometry distance in any one of the far distance examination optical path and the near distance examination optical path so that the optometry distance becomes the optometry distance corresponding to the input optometry distance.

In this application example, a case where the spherical reactive power (hereinafter, referred to as spherical power) and the prismatic amount are changed in accordance with the examination distance and the inter-pupil distance when the examination distance is changed to the desired examination distance will be described as an example. For example, in this application example, the memory 82 stores a table in which the spherical refractive power to be changed, the prismatic amount to be changed, and the optical path to be set are associated with each other (determined) in accordance with the examination distance and the inter-pupil distance.

For example, based on the input examination distance and the inter-pupil distance, the control portion 80 acquires the optical path to be set, the spherical power to be changed, and the prismatic amount to be changed, t from the table stored in the memory 82. Here, for example, the optical path to be set, the spherical power to be changed, and the prismatic amount to be changed in accordance with the examination distance and the inter-pupil distance will be described below.

Figure 9:
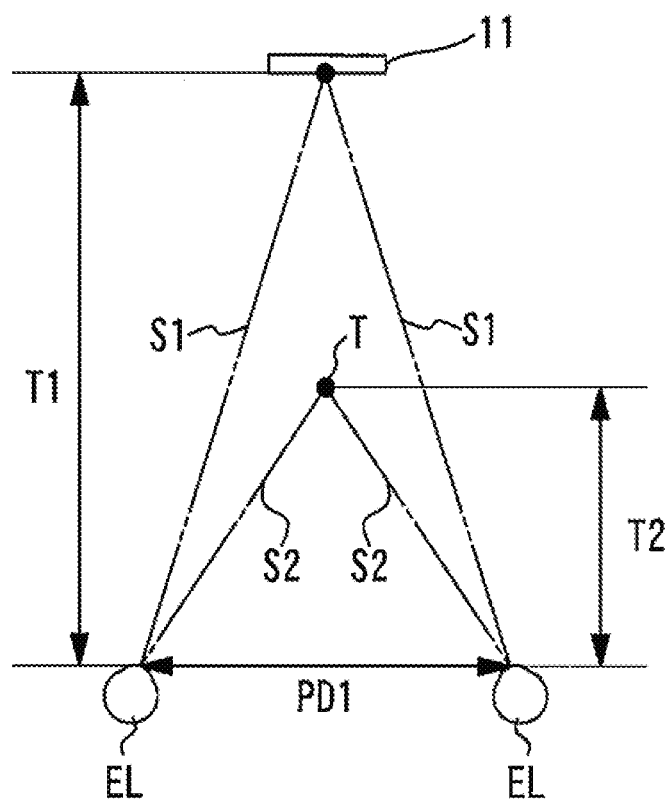
FIG. 9 is a view for describing a configuration for changing an examination distance and an inter-pupil distance.

FIG. 9 is a view for describing a configuration for changing the examination distance and the inter-pupil distance. For example, FIG. 9 illustrates a configuration in which an examinee confirms the visual target presented on the display 11 at an examination distance T1, in which the examination distance and the inter-pupil distance are optically changed so that the visual target presented on the display 11 can be confirmed at an examination distance T2 (the visual target is visible at a position of a point T). For example, in a case where the examinee observes the visual target at the examination distance T1, the visual axis of right and left eyes EL and ER of the examinee is a visual axis S1. For example, in a case where the examinee observes the visual target at the examination distance T2, the visual axis of the right and left subject eyes EL and ER is a visual axis S2. For example, spherical power DI set in order for the visual target to be confirmed at the examination distance T1 to be confirmed at the examination distance T2 for the examinee whose inter-pupil distance of the right and left subject eyes EL and ER is PD1 can be calculated by the following expression (1).

$$D1 = -\left(\frac{1000}{T2} - \frac{1000}{T1}\right) \quad (1)$$

In addition, for example, in order for the examinee whose inter-pupil distance is PD1 to more easily confirm the visual target at the examination distance T2, a prismatic amount Δ1 for changing the visual axis S1 to the visual axis S2 can be calculated by the following expression (2).

$$\Delta 1 = \left(\frac{PD/2}{T2} - \frac{PD/2}{T1}\right) \times 100 \quad (2)$$

As described above, the spherical power and the prismatic amount are calculated in accordance with the examination distance and the inter-pupil distance, and are prepared as the table. In this application example, for example, in a case where the table is prepared, the spherical power calculated by the above-described expression (2) is rounded by a step of 0.25 D (diopter) (calibrated to be a step of 0.25 D). For example, in this application example, in a case where the spherical power calculated by the above-described expression (2) is −0.13 D, the calibration is set as −0.25 D. In addition, for example, in this application example, in a case where the spherical power calculated by the above-described expression (2) is −0.55 D, the calibration is set as −0.75 D. As a matter of course, for example, in a case where the table is prepared, the spherical power is not limited to the above-described configuration in which the calibration is set as the step of 0.25 D). For example, the spherical power may be set using the calculated spherical power, or may be rounded using diopters of different steps. As a matter of course, the same processing as that of the spherical power may be performed on the prismatic amount. In this application example, a configuration for controlling the calculated prismatic amount has been described as an example.

In addition, in this application example, for example, when the examination distance is optically changed in setting the optical path, the optical path is set which can reduce the amount (adding amount of the spherical power and the prismatic amount) of optically changing the visual target. For example, in a case where the spherical power and the prismatic amount which are added to the far distance examination distance in order to present the visual target at the examination distance desired by the examiner are larger than the spherical power and the prismatic amount which are added to the near distance examination distance, the near distance examination optical path for performing the examination at the near distance examination distance is set. In addition, for example, in a case where the spherical power and the prismatic amount which are added to the far distance examination distance in order to present the visual target at the examination distance desired by the examiner are smaller than the spherical power and the prismatic amount which are added to the near distance examination distance, the far distance examination optical path for performing the examination at the far distance examination distance is set. According to this configuration, the optical change amount can be reduced, and the visual target having a more suppressed aberration can be presented.

Hereinafter, changing the examination distance by using the above-described table will be described in more detail. For example, a case will be described where the examiner inputs the examination distance of 30 cm. In this application example, a case where the inter-pupil distance is 64 mm (left eye PD is 32 mm, and right eye PD is 32 mm) will be described as an example. For example, the examiner selects the desired distance examination mode, and inputs 30 cm as the desired distance. If 30 cm is input by the examiner, the control portion 80 acquires change information corresponding to the examination distance of 30 cm and the inter-pupil distance of 64 mm from the table stored in the memory 82.

For example, in a case where the examination distance is 30 cm and the inter-pupil distance is 64 mm, the near distance examination optical path (in this application example, the near distance examination distance in the near distance examination optical path is 40 cm) is set as the optical path. In addition, for example, in a case where the examination distance is 30 cm and the inter-pupil distance is 64 mm, −0.75 D (diopter) is set as the spherical power. In addition, for example, in the case where the examination distance is 30 cm and the inter-pupil distance is 64 mm, BO 4.8Δ is set as the prismatic amount.

For example, the control portion 80 controls the far-near distance switching portion 20 so as to set the optical path to the near distance examination optical path. For example, the control portion 80 moves the display 11 so as to set the optical path through which the image of the target light flux from the display 11 is projected on the subject eye at the near distance examination distance without passing through the concave mirror 13. In a case where the optical path is set to the near distance examination optical path in advance, the spherical power and the prismatic amount are controlled without particularly controlling the far-near distance switching portion 20.

For example, the control portion 80 sets the optical path to the near distance examination optical path, and controls the optometry unit 50 so as to change the spherical power and the prismatic amount.

For example, in a case where the optical path is set to the near distance examination optical path (refer to FIG. 4B), the control portion 80 moves the display 11 together with the holding portion 21 so as to be disposed at the near distance (In this application example, at a distance of 40 cm) from the subject eye E. The target light flux is emitted toward the flat mirror 12 from the display 11. The target light flux is reflected on the flat mirror 12, and is guided to the subject eye E. For example, in a case where the optical path is set to the far distance examination optical path (refer to FIG. 4A), the control portion 80 turns on the display 11. For example, the target light flux is emitted toward the flat mirror 12 from the display 11 held in the holding portion 21. The target light flux is reflected on each of the flat mirror 12 and the concave mirror 13, and is guided again to the subject eye E by way of the flat mirror 12.

For example, the control portion 80 sets the optical path to the near distance examination optical path, and controls the driving portion 54 and the driving portion 55 so that the spherical power is −0.75 D and the prismatic amount is BO 4.8Δ. As in this application example, the respective settings may be simultaneously controlled. As a matter of course, for example, at least two of the setting of the optical path, the setting of the spherical power, and the setting of the prismatic amount may be simultaneously performed. In addition, for example, all settings may be performed at mutually different times.

Here, for example, in a case where the far distance examination optical path is set as the optical path, in order to change the examination distance (5 m in this application example) to the examination distance of 30 cm in the far distance examination optical path, −3.25 D is required as the spherical power, and BO 20.8Δ is required as the prismatic amount. That is, the spherical power and the prismatic amount in a case where the near distance examination optical path is set as the optical path are smaller than the spherical power and the prismatic amount which are added when the far distance examination optical path is set. In this application example, in a case where the examination distance is changed to the examination distance of 30 cm, the near distance examination optical path is set in the configuration. Accordingly, the amount of optically changing the visual target can be reduced, and the visual target having a more suppressed aberration can be presented.

As described above, through the control, the visual target can be presented to the examinee at the examination distance of 30 cm. That is, the examiner can perform the subjective examination at the desired examination distance.

As described above, for example, based on the examination distance information, the subjective optometry apparatus causes the optical path switching portion to set the optical path through which the target light flux is projected on the subject eye to either the first optical path or the second optical path, and moves the distance changing optical member with respect to the set optical path so as to change the examination distance to the examination distance which is different from the first examination distance and the second examination distance. In this manner, the optical path serving as a setting reference can be set in accordance with the examination distance, and the examination distance can be changed by driving the distance changing optical member in the set optical path. Accordingly, the visual target having a suppressed aberration can be presented. Therefore, the visual target under a natural viewing condition can be presented.

In In addition, this application example, for example, the examination distance changing portion may move the distance changing optical member (in this application example, the optical element of the optometry unit 50) so as to change the examination distance to the examination distance which is different from the first examination distance and the second examination distance. In this manner, an easy configuration can change the examination distance.

In addition, in this application example, for example, the distance changing optical member is shared in use with the calibration unit. In this manner, the number of dedicated optical members to be separately provided can be reduced, and complicated calibration processes can be reduced. Therefore, an easy configuration can change the examination distance. In addition, the number of dedicated members is reduced, and thus, the subjective optometry apparatus having a further reduced space can be provided.

As described above, if the examination distance is set, the examination of an examinee starts. For example, in the subjective optometry apparatus 1, the controller 81 is operated by the examiner, and ID of the examinee is input. In this manner, the objective eye refractive power corresponding to the examinee's ID is received from the memory of an objective eye refractive power measurement device (not illustrated). For example, if the objective eye refractive power measurement device receives a patient's ID input from the subjective optometry apparatus 1 from the subjective optometry apparatus 1, the objective eye refractive power corresponding to the patient's ID is retrieved from a memory (not illustrated), and is transmitted to the subjective optometry apparatus 1.

For example, the control portion 80 receives the objective eye refractive power transmitted from the objective eye refractive power measurement device. In this manner, the control portion 80 can acquire the objective eye refractive power of the examinee. For example, if the control portion 80 receives the objective refractive power, the control portion 80 sets the objective refractive power by initializing a value of the subjective examination. That is, the control portion 80 controls the optometry unit 50 so as to set the initial value, based on the near objective eye refractive power. For example, the control portion 80 sets the initial value by setting the calibration power of the optometry unit 50 to a value corresponding to the objective eye refractive power. In this case, for example, the control portion 80 may set the calibration power in view of the spherical power and the prismatic amount which are added in order to optically change the examination distance. In this application example, the spherical power will be described as an example.

For example, in a case where the spherical power is set in order to change the optometry distance, the optometry unit 50 sets the spherical power by adding the spherical power set for changing the optometry distance to the spherical power in the calibration power. As an example, for example, a case where the initial value of the spherical power is −2.00 D and the spherical power for changing the optical distance is −0.75 D will be described as an example. For example, the control portion 80 sets the spherical power to −2.75 D as the initial value. That is, for example, the control portion 80 further adds the spherical power corresponding to −2.00 D as the initial value to −0.75 D set in order to change the optometry distance, and sets −2.75 D as the total spherical power.

In this case, for example, although the corrected spherical power is −2.75 D, −2.00 D is displayed as the corrected spherical power of the controller 81. That is, the spherical power excluding the spherical power for changing the examination distance is displayed. In the above-described configuration, the spherical power has been described as an example. However, this application example is not limited thereto. For example, in a case where the prism is set as the initial value, a process the same as that of the above-described spherical power may be performed. In this way, for example, even in a case where the examination distance is changed using the calibration unit (for example, the optometry unit), the optical characteristics can be changed by the calibration unit in view of the change in the examination distance. Therefore, an easy configuration can change the inspection distance, and the optical characteristics of the target light flux can be satisfactorily changed by the calibration unit.

For example, if the optometry unit 50 is controlled by the control portion 80 and the initial value is completely set, the examiner performs the subjective examination of the subject eye while changing the calibration power of the optometry unit 50 and changing the examination visual target.

For example, at the time of the subjective examination, the examiner operates the controller 81 so as to display the examination visual target on a screen of the display 11. The control portion 80 retrieves the corresponding examination visual target data from the nonvolatile memory 82 in response to the input signal from the controller 81, and controls the display of the display 11. The examination visual target displayed on the display 11 is presented to the subject eye E of the examinee via the examination window 53 in the optometry unit 50 and the presentation window 3. For example, the examiner asks the examinee the visibility of the examination visual targets while switching the examination visual targets. As an example, for example, in a case where the examinee's answer is correct, the examiner switches the visual target to one level higher visual acuity value. In addition, as an example, for example, in a case where the examinee's answer is incorrect, the examiner switches the visual target to one level lower visual acuity value. In addition, for example, the examiner performs the examination while switching the visual targets and changing the calibration degree for the examination visual target displayed on the screen. In this way, the examiner can acquire the subjective eye refractive power (for example, the spherical power S, the astigmatic power C, and the astigmatic axis angle A) of the subject eye at the set examination distance. As a matter of course, the optical characteristics of the subject eye other than the subjective eye refractive power may be acquired by performing the other subjective examination different from the above subjective examination.

For example, if the subjective examination is completely performed at the set examination distance, the examiner performs an examination using a trial frame on the subject eye. For example, the examiner operates an upper switch 8a of the first operation portion 8 so as to raise the optometry unit 50 to the retracted position illustrated in FIGS. 1A and 1B. For example, if the upper switch 8a of the first operation portion 8 is operated, the control portion 80 drives the motor 30. For example, in a case where the optometry unit 50 is moved to the retracted position, the control portion 80 rotates the motor 30 in the rotation direction opposite to the rotation direction of the motor 30 when the optometry unit 50 is moved to the examination position.

For example, if the optometry unit 50 is completely moved to the retracted position, the examiner causes the examinee to wear the trial frame (trial frame or test frame), and checks the examinee's feeling of wearing while replacing the lenses (trial lenses) having different power (trial lens).

For example, in a case where the spherical power set when the examination distance is changed by the examination distance changing portion is high (hyper diopter), display magnification of the visual target to be displayed on the display portion (for example, the display 11) may be changed. In this case, for example, a size of the visual target of the display portion may be changed. In this manner, the visual target under a natural viewing condition can be presented.

1: subjective optometry apparatus
2: housing
3: presentation window
4: holding unit
5: connecting portion
6: movement unit
7: shaft
8: first operation portion
9: second operation portion
10: light projecting optical system
11: display
30: driving portion
31: base
32: block
35: holding arm
36: block receiver
38: support member
39: block receiver
40: observation unit
50: optometry unit
53: examination window
60: corneal position aligning optical system
80: control portion
85: support member

What is claimed is:

1. A subjective optometry apparatus for subjectively measuring optical characteristics of a subject eye, comprising:
    a light projecting optical system that includes a visual target presenting portion configured to emit a target light flux and an optical member configured to guide the target light flux to the subject eye such that an image of the target light flux is optically projected on the subject eye at a first examination distance, and that is configured to project the target light flux emitted from the visual target presenting portion toward the subject eye through the optical member, the light projecting optical system projecting the target light flux on the subject eye at the first examination distance to subjectively measure the optical characteristics of the subject eye;
    an optical path switching portion configured to switch between a first optical path through which the target light flux is projected on the subject eye at the first examination distance and a second optical path through which the image of the target light flux emitted from the visual target presenting portion is projected on the subject eye without passing through the optical member at a second examination distance which is different from the first examination distance;
    an examination distance changing portion that includes a distance changing optical member and a driving portion configured to drive the distance changing optical member, and that is configured to optically change the first examination distance or the second examination distance by driving the distance changing optical member in any one of the first optical path and the second optical path; and
    an examination distance information acquisition portion configured to acquire examination distance information for setting an examination distance set when the target light flux is projected on the subject eye,
    wherein based on the examination distance information, the examination distance changing portion causes the optical path switching portion to set an optical path through which the target light flux is projected on the subject eye to either the first optical path or the second optical path, and drives the distance changing optical member in the set optical path to optically change the examination distance to an examination distance which is different from the first examination distance and the second examination distance.

2. The subjective optometry apparatus according to claim 1,
wherein the examination distance changing portion drives the driving portion to move the distance changing optical member in any one of the first optical path and the second optical path such that the first examination distance or the second examination distance is optically changed.

3. The subjective optometry apparatus according to claim 2,
wherein the examination distance changing portion drives the driving portion to insert the distance changing optical member into the first optical path or the second optical path or to remove the distance changing optical member from the first optical path or the second optical path such that the examination distance is changed.

4. The subjective optometry apparatus according to claim 2,
wherein the examination distance changing portion drives the driving portion to move the distance changing optical member in an optical axis direction of the first optical path or the second optical path such that the examination distance is changed.

5. The subjective optometry apparatus according to claim 1,
wherein the distance changing optical member is at least any one of a lens and a prism.

6. The subjective optometry apparatus according to claim 1, further comprising:
a calibration unit that is disposed in the optical path of the light projecting optical system and that is configured to change optical characteristics of the target light flux;
an optical characteristic information acquisition portion configured to acquire optical characteristic information for causing the calibration unit to change the optical characteristics of the target light flux; and
a calibration control portion configured to control the calibration unit based on the optical characteristic information.

7. The subjective optometry apparatus according to claim 6,
wherein the distance changing optical member is shared in use with the calibration unit.

8. The subjective optometry apparatus according to claim 7,
wherein the calibration control portion controls the calibration unit based on the optical characteristic information and the examination distance information.

9. The subjective optometry apparatus according to claim 6, further comprising:
a housing that accommodates the light projecting optical system; and
a holding unit that holds the calibration unit,
wherein the holding unit integrally connects the housing and the calibration unit.

10. The subjective optometry apparatus according to claim 1,
wherein in setting the first optical path or the second optical path, the examination distance changing portion sets an optical path having a smaller amount of an optical change obtained when the first examination distance or second examination distance is changed by the distance changing optical member.

11. The subjective optometry apparatus according to claim 1,
wherein the first examination distance is a far distance examination distance, and
the second examination distance is a near distance examination distance.

12. The subjective optometry apparatus according to claim 1,
wherein the examination distance changing portion drives the distance changing optical member to change at least spherical refractive power such that the examination distance is optically changed to an examination distance which is different from the first examination distance and the second examination distance.

13. The subjective optometry apparatus according to claim 1,
wherein the optical path switching portion switches between the first optical path and the second optical path by inserting or removing the visual target presenting portion between the subject eye and the optical member in the first optical path.

14. The subjective optometry apparatus according to claim 1, wherein the examination distance changing portion and the optical path switching portion are separate mechanisms.

15. The subjective optometry apparatus according to claim 14,
wherein the examination distance changing portion changes a lens in an examination window of an optometry unit in order to optically change the first examination distance or the second examination distance; and
wherein the optical path switching portion changes a position of the visual target presenting portion to switch between the first optical path and the second optical path.

16. A non-transitory computer readable recording medium storing a subjective optometry program used in a subjective optometry apparatus for subjectively measuring optical characteristics of a subject eye by causing a light projecting optical system to project a target light flux on the subject eye at a first examination distance,
wherein the subjective optometry apparatus includes:
the light projecting optical system that includes a visual target presenting portion configured to emit the target light flux and an optical member configured to guide the target light flux to the subject eye such that an image of the target light flux is optically projected on the subject eye at the first examination distance, and that is configured to project the target light flux emitted from the visual target presenting portion toward the subject eye through the optical member;
an optical path switching portion configured to switch between a first optical path through which the target light flux is projected on the subject eye at the first examination distance and a second optical path through which the image of the target light flux emitted from the visual target presenting portion is projected on the subject eye without passing through the optical member at a second examination distance which is different from the first examination distance;
a distance changing optical member; and
a driving portion configured to drive the distance changing optical member,
wherein the subjective optometry program is executed by a processor of the subjective optometry apparatus to cause the subjective optometry apparatus to execute:

an examination distance information acquisition step of acquiring examination distance information for setting an examination distance set when the target light flux is projected on the subject eye; and an examination distance change step of optically changing the first examination distance or the second examination distance by driving the distance changing optical member in any one of the first optical path and the second optical path, wherein in the examination distance change step, based on the examination distance information, the optical path switching portion sets an optical path through which the target light flux is projected on the subject eye to either the first optical path or the second optical path, and drives the distance changing optical member in the set optical path to optically change the examination distance to an examination distance which is different from the first examination distance and the second examination distance.

* * * * *